US008034331B2

(12) United States Patent
Wang et al.

(10) Patent No.: US 8,034,331 B2
(45) Date of Patent: Oct. 11, 2011

(54) METHOD OF DELIVERY OF NUCLEIC ACIDS TO PERIPHERAL NEURONS

(75) Inventors: Shu Wang, Singapore (SG); Xu Wang, Halifax (CA)

(73) Assignee: Agency for Science, Technology and Research, Singapore (SG)

(*) Notice: Subject to any disclaimer, the term of this patent is extended or adjusted under 35 U.S.C. 154(b) by 368 days.

(21) Appl. No.: 11/795,348

(22) PCT Filed: Jan. 20, 2005

(86) PCT No.: PCT/SG2005/000015
§ 371 (c)(1),
(2), (4) Date: Apr. 15, 2008

(87) PCT Pub. No.: WO2006/078221
PCT Pub. Date: Jul. 27, 2006

(65) Prior Publication Data
US 2008/0318882 A1    Dec. 25, 2008

(51) Int. Cl.
*A61K 48/00* (2006.01)
*A01N 63/00* (2006.01)
(52) U.S. Cl. ..................... 424/93.2; 514/44 A
(58) Field of Classification Search .......... None
See application file for complete search history.

(56) References Cited

U.S. PATENT DOCUMENTS

| | | | |
|---|---|---|---|
| 5,019,087 A | 5/1991 | Nichols | |
| 5,168,062 A | 12/1992 | Stinski | |
| 5,584,885 A | 12/1996 | Seckel | |
| 5,849,522 A | 12/1998 | Fleckenstein et al. | |
| 2004/0121958 A1 | 6/2004 | O'Brien | |
| 2004/0197313 A1 | 10/2004 | Wang et al. | |

OTHER PUBLICATIONS

Goss et al. Herpes-Simplex Mediated Gene Transfer of Nerve Growth Factor Portects Against Peripheral Neuropathy in Streptozotocin-Induced Diatbetes in the Mouse. Diabetes, 2002, vol. 51, pp. 2227-2232.*
Finegold et al. A Paracrine Paradigm for in Vivo Gene Therapy in the Central Nervous System: Treatment for Chronic Pain. Human Gene Therapy, 1999, vol. 10, pp. 1251-1257.*
Becker et al. Uses of Recombinant Adevovirus in Metabolic Engineering Methods in Cell Biology, 1994, vol. 43, pp. 161-189.*
Glatzel et al. Adenoviral and Adeno-Assocated Viral Transfer of Genes to the Peripheral Nervous System. Proced. Natl. Acad. Sci, 2000, vol. 97, pp. 442-447.*
Tang et al. Polyethylene Glycol Modified Polyethyleneimine for Improved CNS Gene Transfer: Effects of PEGylation Extent. Biomaterials, 2003, vol. 24, pp. 2351-2362.*
Federoff et al. Expression of Nerve Growth Factor In Vivo from a Defective Herpes Simplex Virus 1 Vectora Prevents Effects of Axotomy on Sympathetic Ganglia. Proceed. Natl. Acad. Sci., 1992, vol. 89, pp. 1636-1640.*
Yamashhita et al. Effect on Motor Neuron Survival in Mutant SOD1 (G93A) Transgenic Mice by Bcl-2 Expression using Retrograde Axonal Transport of Adenoviral Vectors. Neurosci. Letters, 2002, vol. 328, pp. 289-293.*
Blits et al. Adeno-Associated Viral Vector Mediated Neurotrophin Gene Transfer in the Injured Adult Rat Spinal Cord Imporves Hin-Limb Functioln. Neurosci., 2003, vol. 118, pp. 271-281.*
Fenrich, K. and Gordon, T., "Axonal Regeneration in the Peripheral and Central Nervous Systems—Current Issues and Advances", The Canadian Journal of Neurological Sciences, May 2004, pp. 142-156, vol. 31, No. 2.
Schmidt, C.E. and Leach, J.B., "Neural Tissue Engineering; Strategies for repair and regeneration", Annual Review of Biomedical Engineering, Aug. 2003, pp. 293-347, vol. 5.
Williams, L.R. et al., "Exogenous Matrix Precursors Promote Functional Nerve Regeneration Across a 15-mm Gap Within a Silicone Chamber in the Rat", The Journal of Comparative Neurology, 1987, pp. 284-290, vol. 264.
Terenghi, G., "Peripheral nerve regeneration and neurotrophic feactors", Journal of Anatomy, Jan. 1999, pp. 1-14, vol. 194 (Part 1).
Krummenacher, C. et al., "Cellular Localization of Nectin-1 and Glycoprotein D during Herpes Simplex Virus Infection", Aug. 2003, pp. 8985-8999, vol. 77, No. 16.
Sarkis, C. et al., "Efficient transduction of neural cells in vitro and in vivo by a baculovirus-derived vector", Proceedings of the National Academy of Sciences of the United States of America, Dec. 19, 2000, pp. 14638-14643, vol. 97, No. 26.
Ghosh, S. et al., "Baculovirus as Mammalian Cell Expression Vector for Gene Therapy: An Emerging Strategy", Molecular Therapy, Jul. 2002, pp. 5-11, vol. 6, No. 1.
Kost, T.A. and Condreay, J.A., "Recombinant baculoviruses as mammalian cell gene-delivery vectors", Trends in Biotechnology, Apr. 2002, pp. 173-180, vol. 20, No. 4.
Tani, H. et al., "In Vitro and In Vivo Gene Delivery by Recombinant Baculoviruses", Journal of Virology, Sep. 2003, pp. 9799-9808, vol. 77, No. 18.
Lehtolainen, P. et al., "Baculoviruses exhibit restricted cell type speciftcty in rat brain: a comparison of baculovirus- and adenovirus-mediated intracerebral gene transfer in vivo", Gene Therapy, Dec. 2002, pp. 1693-1699, vol. 9, No. 24.
Tani, H. et al., "Characterization of Cell-Surface Determinants Important for Baculovirus Infection", Virology, Jan. 5, 2001, pp. 343-353, vol. 279, Issue 1.
Huser, A. et al., "Incorporation of decay-accelerating factor into the baculovirus envelope generates complement-resistant gene transfer vectors", Nature Biotechnology, May 2001, pp. 451-455, vol. 19.
Boussif, O. et al., "A versatile vector for gene and oligonucleotide transfer into cells in culture and in vivo: Polyethylenimine", Proceedings of the National Academy of Sciences of the United States of America, Aug. 1, 1995, pp. 7297-7301, vol. 92, No. 16.

(Continued)

*Primary Examiner* — Deborah Crouch
(74) *Attorney, Agent, or Firm* — Klarquist Sparkman, LLP

(57) ABSTRACT

The invention provides for methods for delivering a nucleic acid into a peripheral neuron by identifying a target neuron in a dorsal root ganglion and intrathecally delivering a vector comprising the nucleic acid to the dorsal root ganglion neuron. The nucleic acid may encode a neurotrophic factor that may be used to treat a peripheral neuropathy or, in conjunction with a nerve guide conduit, to treat a transected peripheral nerve.

18 Claims, 8 Drawing Sheets

OTHER PUBLICATIONS

Knight, A. et al., "Non-viral neuronal gene delivery mediated by the HC fragment of tetanus toxin", European Journal of Biochemistry, Feb. 1999, pp. 762-769, vol. 259, Issue 3.

Chevalier-Mariette, C. et al., "CpG content affects gene silencing in mice: evidence from novel transgenes", Genome Biology, 2003, vol. 4, Issue 9, Article R53.

Brooks, A.R. et al., "Transcriptional silencing is associated with extensive methylation of teh CMV promoter following adenoviral gene delivery to muscle", The Journal of Gene Medicine, 2004, pp. 395-404, vol. 6.

Abdallah, B. et al., "A Powerful Nonviral Vector for in Vivo Gene Transfer into the Adult Mammalian Brain: Polyethylenimine", Human Gene Therapy, Oct. 1996, pp. 1947-1954, vol. 7, No. 16.

Shi, L. et al., "Repeated intrathecal administration of plasmid DNA complexed with polyethylene glycol-grafted polyethylenimine led to prolonged transgene expression in the spinal cord", Gene Therapy, 2003, pp. 1179-1188, vol. 10.

Sasahara, M. et al., "PDGF B-Chain in Neurons of the Central Nervous System, Posterior Pituitary, and in a Transgenic Model", Cell, Jan. 11, 1991, pp. 217-227, vol. 64.

Gorman, C.M. et al., "The Rous sarcoma virus long terminal repeat is a strong promoter when introduced into a variety of eukaryotic cells by DNA-mediated transfection", Proceedings of the National Academy of Sciences of the United States of America, Nov. 1982, pp. 6777-6781, vol. 79.

Ghosh, P.R. et al., "Identification of a promoter component involved in positioning the 5' termini of simian virus 40 early mRNAs", Proceedings of the National Academy of Sciences of the United States of America, Jan. 1981, pp. 100-104, vol. 78, No. 1.

Boshart, M. et al., "A Very Strong Enhancer is Located Upstream of an Immediate Early Gene of Human Cytomegalovirus", Cell, Jun. 1985, pp. 521-530, vol. 41.

Niwa, H. et al., "Efficient selection for high-expression transfectants with a novel eukaryotic vector", Gene, Dec. 15, 1991, pp. 193-200, vol. 108, Issue 2.

Smith, T.F. and Waterman, M.S., "Comparison of Biosequences", Advances in Applied Mathematics, 1981, pp. 482-489, vol. 2.

Needleman, S.B. and Wunsch, C.D., "A General Method Applicable to the Search for Similarities in the Amino Acid Sequence of Two Proteins", Journal of Molecular Biology, Mar. 28, 1970, pp. 443-453, vol. 48, Issue 3.

Pearson, W.R. and Lipman, D.J., "Improved tools for biological sequence comparison", Proceedings of the National Academy of Sciences of the United States of America, Apr. 15, 1988, pp. 2444-2448, vol. 85, No. 8.

Altschul, S.F. et al., "Basic Local Alignment Search Tool", Journal of Molecular Biology, Oct. 5, 1990, pp. 403-410, vol. 215, Issue 3.

Yamamori, T. et al., "The Cholinergic Neuronal Differentiation Factor from Heart Cells Is Identical to Leukemia Inhibitory Factor", Science, Dec. 15, 1989, pp. 1412-1416, vol. 246, No. 4936.

Lee, M. et al., "FK506 promotes functional recovery in crushed rat sciatic nerve", Muscle & Nerve, Apr. 2000, pp. 633-640, vol. 23.

Kishi, M. et al., "Morphometry of Dorsal Root Ganglion in Chronic Experimental Diabetic Neuropathy", Diabetes, Mar. 2002, pp. 819-824, vol. 51, Issue 3.

England, J.D. and Asbury, A.K., "Peripheral neuropathy", The Lancet, Jun. 26, 2004, pp. 2151-2161, vol. 363, Issue 9427.

Stoll, G. and Muller, H.W., "Nerve Injury, Axonal Degeneration and Neural Regeneration: Basic Insights", Brain Pathology, Apr. 1999, pp. 313-325, vol. 9, Issue 2.

Glorioso, J.C. et al., "Gene Therapy for Chronic Pain", Current Opinion in Molecular Therapeutics, Oct. 2003, pp. 483-488, vol. 5, Issue 5.

Hasse, G. et al., "Adenovirus-mediated transfer of the neurotrophin-3 gene into skeletal muscle of pmn mice: Therapeutic effects and mechanisms of action", Journal of the Neurological Sciences, Oct. 1, 1998, pp. S97-S105, vol. 160, Supplement 1.

Jackson, C.A. et al., "Gene expression in the muscle and central nervous system following intramuscular inoculation of encapsidated or naked poliovirus replicons", Virology, Sep. 15, 2003, pp. 45-61, vol. 314, Issue 1.

Goss, Jr et al., "Antinociceptive effect of a genomic herpes simplex virus-based vector expressing human proenkephalin in rat dorsal root ganglion", Gene Therapy, Apr. 2001, pp. 551-556, vol. 8, Issue 7.

Glatzel, M. et al., "Adenoviral and adeno-associated viral transfer of genes to the peripheral nervous system", Proceedings of the National Academy of Sciences of the United States of America, Jan. 4, 2000, pp. 442447, vol. 97, Issue 1.

Xu, X. et al., "Peripheral nerve regeneration with sustained release of poly(phosphoester) microencapsulated nerve growth factor within nerve guide conduits", Biomaterials, Jun. 2003, pp. 2405-2412, vol. 24, Issue 13.

Jackson, C.A. et al., "Repetitive Intrathecal Injections of Poliovirus Replicons Result in Gene Expression in Neurons of the Central Nervous System Without Pathogenesis", Human Gene Therapy, Oct. 2001, pp. 1827-1841, vol. 12, No. 15.

Hudson, T.W. et al., "Engineering Strategies for peripheral nerve repair", Clinics in Plastic Surgery, Oct. 1999, pp. 617-628, vol. 26, Issue 4.

Liu, B.H. et al., "CMV enhancer/human PDGF-beta promoter for neuron-specific transgene expression", Gene Therapy, Jan. 2004, pp. 52-60, vol. 11, Issue 1.

Zeng, J. et al., "A synthetic peptide containing loop 4 of nerve growth factor for targeted gene delivery", The Journal of Gene Medicine, Nov. 2004, pp. 1247-1256, vol. 6, Issue 11.

Thorne, R.G. and Frey III, W.H., "Delivery of Neurotrophic Factors to the Central Nervous System: Pharmacokinetic Considerations", Clinical Pharmacokinetics, 2001, pp. 907-946, vol. 40, No. 12.

Friede, R.L. and Bischhausen, R., "How are sheath dimensions affected by axon caliber and internode length?", Brain Research, Mar. 11, 1982, pp. 335-350, vol. 235, Issue 2.

Mannes, A.J. et al., "Adenoviral gene transfer to spinal cord neurons: intrathecal vs. intraparenchymal administration", Brain Research, May 18, 1998, pp. 1-6, vol. 793, Issues 1-2.

Liu, Y. et al., "Application of recombinant adenovirus for in vivo gene delivery to spinal cord", Brain Research, Sep. 12, 1997, pp. 19-29, vol. 768, Issues 1-2.

Xu. Y. et al., "Efficiencies of Transgene Expression in Nociceptive Neurons Through Different Routes of Delivery of Adeno-Associated Viral Vectors", Human Gene Therapy, Jun. 2003, pp. 897-906, vol. 14, No. 9.

Davar, G. et al,. "Gene Delivery to Rat Sensory Ganglia and Spinal Cord Cells Using Herpes Virus Vectors", Society for Neuroscience Abstracts, 1991, p. 1004, vol. 17, Issues 1-2.

Barrett, L.B. et al., "Developing a cytoplasmic expression system for delivering neurotrophic factors (NTF) to adult dorsal root ganglion neurons (DRGN)", Society for Neuroscience Abstracts, 2001, p. 2039, vol. 27, Issue 2.

Bledsoe, A.W. et al., "Targeted foreign gene expression in spinal cord neurons using poliovirus replicons", Journal of Neurovirology, 2000, pp. 95-105, vol. 6, No. 2.

Palmer, J.A. et al., "Development and Optimization of Herpes Simplex Virus Vectors for Multiple Long-Term Gene Delivery to the Peripheral Nervous System", Journal of Virology, Jun. 2000, pp. 5604-5618, vol. 74, Issue 12.

Xu, Y. et al., "Adeno-associated viral transfer of opioid receptor gene to primary sensory neurons: A strategy to increase opioid antinociception", Proceedings of the National Academy of Sciences of the United States of America, May 13, 2003, pp. 6204-6209, vol. 100, No. 10.

Mata, M. et al., "Targeted gene delivery to the nervous system using herpes simplex virus vectors", Physiology & Behaviour, Dec. 2002, pp. 483-488, vol. 77, Issues 4-5.

Goldstein, M.E. et al., "mRNA levels of all three neurofilament proteins decline following nerve transection", Molecular Brain Research, Jun. 1988, pp. 287-292, vol. 3, Issue 3.

Hefti, F. et al., "Chronic Intraventricular Injections of Nerve Growth Factor Elevate Hippocampal Choline Acetyltransferase Activity in Adult Rats with partial Septo-Hippocampal Lesions", Brain Research, Feb. 20, 1984, pp. 305-311, vol. 293, Issue 2.

Levi-Montalcini, R., "The Nerve Growth Factor 35 Years Later", Science, Sep. 4, 1987, pp. 1154-1162, vol. 237, No. 4819.

Martino, G. et al., "The ependymal route to the CNS: an emerging gene-therapy approach for MS", Trends in Immunology, Sep. 1, 2001, pp. 483-490, vol. 22, No. 9.

Mobley, W.C. et al., "Choline Acetyltransferase Activity in Striatum of Neonatal Rats Increased by Nerve Growth Factor", Science, Jul. 19, 1985, pp. 284-287, vol. 229, No. 4710.

Muller, H. et al., "Nerve regeneration chamber: evaluation of exogenous agents applied by multiple injections", Brain Research, Jun. 16, 1987, pp. 320-326, vol. 413, Issue 2.

Rich, K.M. et al., "Nerve growth factor protects adult sensory neurons from cell death and atrophy caused by nerve injury", Journal of Neurocytology, Apr. 1987, pp. 261-268, vol. 16, No. 2.

Rich, K.M. et al., "Nerve Growth Factor Enhaners Regeneration through Silicone Chambers", Experimental Neurology, Aug. 1989, pp. 162-170, vol. 105, Issue 2.

Saika, T. et al., "Effects of nerve crush and transection on mRNA levels (or nerve growth factor receptor in the rat facial motoneurons", Molecular Brain Research, Jan. 1991, pp. 157-160, vol. 9, Issues 1-2.

Yao, M.Z. et al., "Adenovirus-mediated interleukin-2 gene therapy of nociception", Gene Therapy, Aug. 2003, pp. 1392-1399, vol. 10, No. 16.

Lai, J. et al., "Inhibition of neuropathic pain by decreased expression of the tetrodotoxin-resistant sodium channel, NaV1.8", Pain, Jan. 1, 2002, pp. 143-152, vol. 95, No. 1-2.

Goss, J.R., "Herpes Simplex-Mediated Gene Transfer of Nerve Growth Factor Protects Against Peripheral Neuropathy in Streptozotocin-Induced Diabetes in the Mouse", Diabetes, Jul. 2002, pp. 2227-2232, vol. 51, No. 7.

Glorioso, JC et al., "Therapeutic gene transfer to the nervous system using viral vectors", Journal of NeuroVirology, Apr. 2003, pp. 165-172, vol. 9, No. 2.

Schmidt, C.E. and Leach, J.B., "Neural Tissue Engineering: Strategies for Repair and Regeneration", Annual Review of Biomedical Engineering, pp. 293-347, vol. 5.

Wang, X. et al., "Gene Transfer to Dorsal Root Ganglia by Intrathecal Injection: Effects on Regeneration of Peripheral Nerves", Molecular Therapy, Aug. 1, 2005, pp. 314-320, vol. 12, No. 2.

First Examination Report issued in corresponding European Patent Application No. 05704835.7 dated Oct. 8, 2010.

* cited by examiner

SEQUENCE LISTING

```
<160> NUMBER OF SEQ ID NOS: 4

<210> SEQ ID NO 1
<211> LENGTH: 28
<212> TYPE: DNA
<213> ORGANISM: artificial
<220> FEATURE:
<223> OTHER INFORMATION: synthetic primer

<400> SEQUENCE: 1
attgcggccg cggtaccgag ctcttacg                                            28

<210> SEQ ID NO 2
<211> LENGTH: 32
<212> TYPE: DNA
<213> ORGANISM: artificial
<220> FEATURE:
<223> OTHER INFORMATION: synthetic primer

<400> SEQUENCE: 2
attgcggccg cttatcgatt ttaccacatt tg                                       32

<210> SEQ ID NO 3
<211> LENGTH: 20
<212> TYPE: DNA
<213> ORGANISM: artificial
<220> FEATURE:
<223> OTHER INFORMATION: synthetic primer

<400> SEQUENCE: 3
attgctcaac agtatgggca                                                     20

<210> SEQ ID NO 4
<211> LENGTH: 21
<212> TYPE: DNA
<213> ORGANISM: artificial
<220> FEATURE:
<223> OTHER INFORMATION: synthetic primer

<400> SEQUENCE: 4
cgaagaagga gaatagggtt g                                                   21
```

METHOD OF DELIVERY OF NUCLEIC ACIDS TO PERIPHERAL NEURONS

FIELD OF THE INVENTION

The present invention relates generally to compositions and methods for delivering nucleic acids to peripheral neurons.

BACKGROUND OF THE INVENTION

Nerve regeneration is a complex biological process. The degenerative processes following damage to nerves in the central and peripheral nervous system are similar in some respects but different in others. One of the largest differences is that peripheral nerves have a much greater capacity to regenerate their axons following nerve injury (Fenrich, K. et al. 2004, *Can J Neurol Sci.* 31(2):142).

Schmidt and Leach (2003, *Annu. Rev. Biomed. Eng.* 5:293) have recently reviewed a number of ways of treating nerve injuries. Current treatments for injury-induced nerve defects typically rely on donor tissues obtained from the patient. This has raised the issues of loss of function at the donor sites, formation of potentially painful neuromas, structural differences between donor and recipient nerves and a shortage of graft material for extensive repair. To circumvent these problems, synthetic nerve guide conduits (NGCs) have been developed to bridge the nerve gaps by securing the severed nerve stumps into the two ends of the conduit (U.S. Pat. No. 5,019,087). A number of devices, such as, for example, Integra Neurosciences Type I collage tube and SaluMedica's SaluBridge™ Nerve Cuff have been approved by the US Food and Drug Agency. These devices, however, are reserved for treatment of relatively short nerve defects, and in most cases the synthetic conduits do not function as well as nerve autografts (Schmidt & Leach 2003, *Annu. Rev. Biomed. Eng.* 5:293).

Several tissue-engineering approaches have been proposed to enhance the performance of NGCs, which include delivering neurotrophic factors within hollow tubes. Filling silicone NGCs with dialyzed plasma resulted in a three to fivefold increase in functional restitution at eight weeks compared to NGCs filled with phosphate buffered saline (Williams et al. 1987, *J. Comparative Neurology* 264:284). Alternatively, neurotrophic factors such as nerve growth factor (NGF), brain-derived neurotrophic factor (BDNF), fibroblast growth factor (FGF), glial growth factor (GFG) and ciliary neurotrophic factor (CNTF) delivered within a conduit may significantly increase the morphological and/or functional recovery of transected and repaired nerves.

NGF is the first and best-characterized nerve-derived factor and acts on a relatively limited variety of neuronal populations, including sympathetic, subpopulations of sensory neurons of peripheral nervous system and striatal and septal cholinergic neurons in the brain (Terenghi, G. 1999, *J. Anat* 194:1-14). In normal circumstances, NGF is present at a very low concentration but rapidly increases in the experimental nerve injury animal model. NGF is produced mainly by the target tissue and Schwann cells in the distal stump of damaged nerves and then transported in a retrograde manner to the cell soma before acting on receptors on neurons and producing the neurotrophic effects. In peripheral neuropathies, such transport within diseased nerves may be affected, being reduced or totally blocked. While delivery of NGF promotes nerve regeneration within conduits at an early stage, the promoting effect may not last after one month, probably due to the rapid decline of NGF concentrations in the conduit caused by the degradation in aqueous media at 37° C., leakage from the conduit and/or dilution by entering fluids. Furthermore, the timing of the introduction of neurotrophic factors into NGCs has a significant influence on the healing or regenerative processes: introducing various agents too early or too late may inhibit the regenerative process (U.S. Pat. No. 5,584,885).

The cell bodies of sensory neurons are located in dorsal root ganglia (DRG), nodules at the distal end of the dorsal root of each spinal nerve. Within the dural sheath and surrounded by the cerebral spinal fluid (CSF), dorsal and ventral nerve roots leave through the intervertebral foramen, where the dorsal root forms the dorsal root ganglion and thereafter joins the ventral root to form the spinal nerve root. Morphologically, a somatosensory neuron in DRG has a unipolar structure, with a connection to the central nervous system (CNS) by a long ascending axon within the spinal cord, and to the peripheral nervous system (PNS) by a second axon branch descending through the spinal nerve root and further out into a peripheral nerve. Functionally, DRG neurons are heterogeneous, signaling receptor-transduced stimuli of diverse sensory modalities that range from touch, temperature, pain to proprioception.

SUMMARY OF THE INVENTION

In one aspect the invention provides a method of delivering a nucleic acid into a neuronal cell in the peripheral nervous system of a host comprising the step of identifying a target neuronal cell in a dorsal root ganglion and administering a vector comprising the nucleic acid into a site in the cerebrospinal fluid of the host wherein the site is sufficiently proximal to the dorsal root ganglion to deliver the nucleic acid into the cell body of the target neuronal cell.

In another aspect the invention provides a method of treating a peripheral neuropathy in a host, the method comprising identifying a target neuronal cell in a dorsal root ganglion affected by the neuropathy, and administering a vector comprising a therapeutic nucleic acid into a site in the cerebrospinal fluid of the host wherein the site is sufficiently proximal to the dorsal root ganglion to deliver the nucleic acid into the cell body of the target neuronal cell.

In another aspect the invention provides a method of treating a transected peripheral nerve having a proximal and a distal stump in a host, the method comprising intrathecally administering a vector comprising a therapeutic nucleic acid to a dorsal root ganglion neuronal cell wherein the distal and proximal stumps are secured to a nerve guide conduit.

In another aspect the invention provides a use of a vector comprising a nucleic acid to deliver the nucleic acid into a target neuronal cell in a dorsal root ganglion wherein said delivery is effected from a site of administration of the vector in the cerebrospinal fluid which is sufficiently proximal to the dorsal root ganglion to deliver the nucleic acid into the cell body of the target neuronal cell.

In yet another aspect the invention provides a use of a vector comprising a therapeutic nucleic acid to treat a peripheral neuropathy in a host wherein the nucleic acid is delivered into a target neuronal cell in a dorsal root ganglion affected by the neuropathy from a site of administration of the vector in the cerebrospinal fluid which is sufficiently proximal to the dorsal root ganglion to deliver the nucleic acid into the cell body of the target neuronal cell.

In still yet another aspect, the invention provides a use of a vector comprising a therapeutic nucleic acid to treat a transected peripheral nerve having a proximal stump and a distal stump in a host wherein the proximal and distal stumps are secured to a nerve guide conduit and wherein the nucleic acid is delivered from a site of administration in the cerebrospinal fluid to a dorsal root ganglion neuronal cell.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention:

FIG. 3C depicts the time-dependent change of luciferase activity, expressed in RLU per milligram of protein, in DRG after intrathecal injection of PEI/DNA complexes.

DETAILED DESCRIPTION

Figure 1:
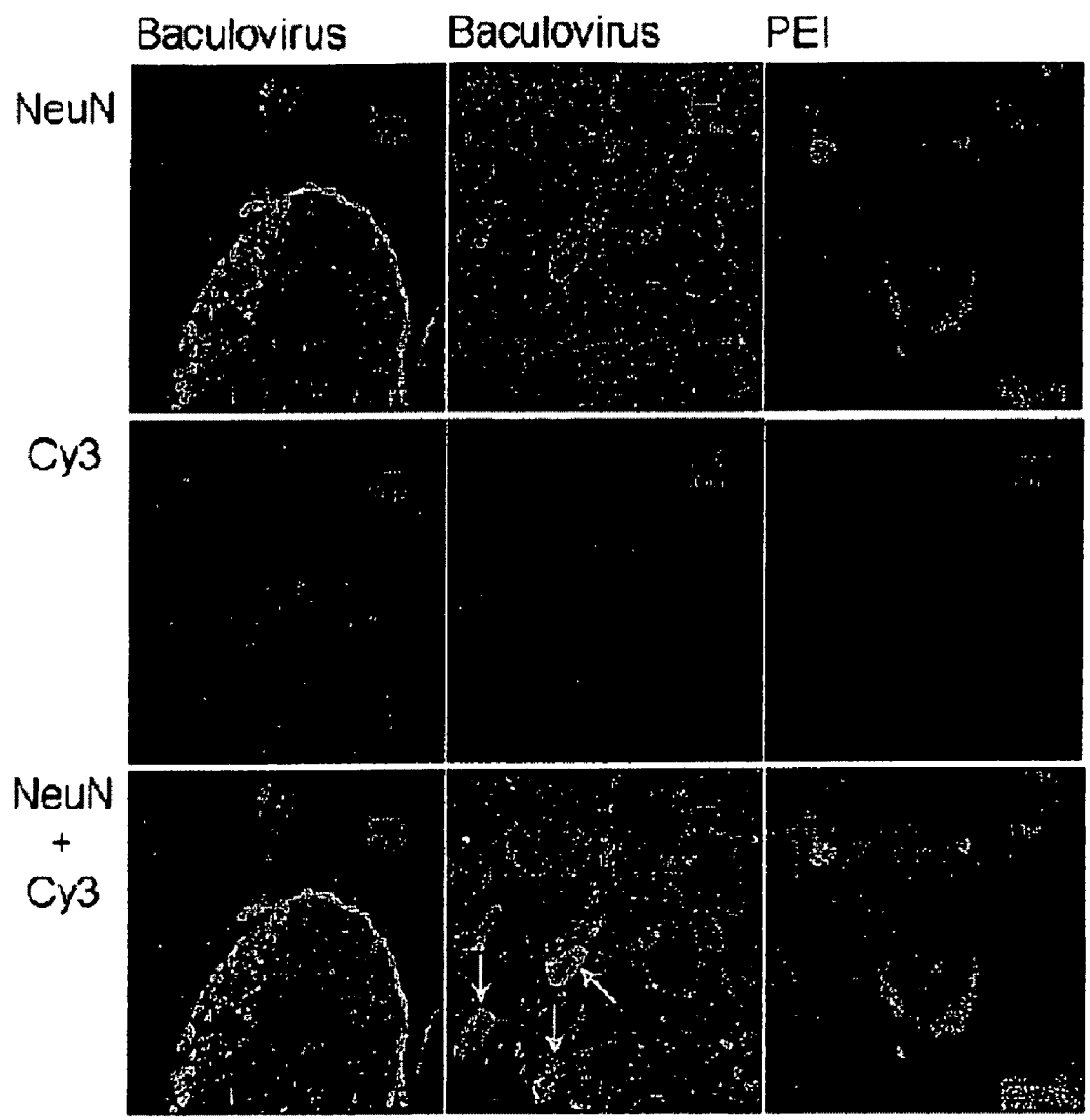
FIG. 1 shows confocal scanning microscope images of Cy3 labeled baculoviruses or PEI/DNA complexes in rat DRG at 2 days post-injection. The DRG neurons are stained with FITC-labeled NeuN (green). Cy3 labeled baculoviruses and PEI complexes (red) are found mainly in the cytoplasm of cells and well co-localized with NeuN signals (arrows)

The inventors have surprisingly discovered that the administration of nucleic acid vectors into cerebrospinal fluid surrounding the spinal chord is an effective way of delivering exogenous nucleic acids into the soma of neurons in dorsal root ganglia. More specifically, nucleic acid vectors encoding NGF intrathecally injected into cerebrospinal fluid were to shown to positively influence the regeneration of a transected sciatic nerve within a nerve guide conduit.

The terms "neuronal cell" and "neuron", which are use interchangeably herein, in accordance with the usual meaning in the art, refer to any conducting cell of the nervous system, which typically includes the cell body or soma, several dendrites and an axon. The terms include a single cell as well as a plurality or population of cells unless the context clearly indicates otherwise.

The intrathecal administration of recombinant vectors into the cerebrospinal fluid proximal to a dorsal root ganglion allows for the transfection of dorsal root ganglion neuronal cells in a manner that may be independent of axonal transport and may be accomplished by relatively minimally invasive techniques. Following peripheral nerve injury, cells and tissues surrounding the injury site, including Schwann cells, normally secrete factors that are taken up by the axon of the injured or damaged neuron. These factors are generally transported to the soma of the injured nerve by axonal transport, where they interact with receptors and exert biological effects. A number of viral-based gene therapy system, including herpes and poliovirus based therapies, have exploited this axonal transport to deliver therapeutic genes to otherwise inaccessible neurons, including those within the central nervous system. As would be appreciated by a person skilled in the art, these approaches may provide less than optimal gene delivery in circumstances where axonal transport is compromised, such as, for example, in certain neuropathies, such as, for example, diabetic neuropathy and peripheral nerve injuries caused by trauma, compression or transection.

By using intrathecal injection to target DRG neurons, nucleic acid vectors encoding exogenous genes under the control of an appropriate promoter may be delivered to the soma of cells in the DRG in circumstances where peripheral axonal transport is compromised or abolished. Therefore, a nucleic acid may be delivered to a neuronal cell body in the peripheral nervous system by the administration of a vector comprising the nucleic acid into cerebrospinal fluid. As will be understood, the site of injection in the cerebrospinal fluid will depend on the specific target neuronal cells of a dorsal root ganglia into which the delivery of a nucleic acid is desired. More specifically, the site of administration may be selected to be sufficiently proximal to the target DRG neuronal cells to deliver the nucleic acid into the cell body of the targeted cells, meaning, the delivery can be mediated or effected independently of axonal transport. Therefore, nucleic acids may be delivered to target cells independent of axonal transport. A person skilled in the art would appreciate, from the segmental architecture of the peripheral nervous system, that the site of administration will depend on which DRG nerve cells are targeted for transfection. For example, in order to deliver a transgenic gene product to peripheral nerves extending into in the index finger of a subject, the vector is preferably intrathecally administered into the CSF surrounding or near the C6 vertebrae of the subject. Appropriate sites of injection may be determined by reference common anatomy texts, such as, for example, *Introduction to Human Anatomy* $6^{th}$ edition, Francis, C. V. Mosby Company, 1973.

In a specific embodiment, the vector is administered by lumbar injection. Lumbar injection is considered safe and poses little danger of injuring the spinal cord and nerve roots, as cerebrospinal fluid (CSF) in the relatively wide subarachnoid space at the level of the cauda equina allows a certain degree of mobility of the nerve roots in response to needle puncture. This method would therefore permit safe multiple administrations for gene delivery to lumbar DRGs. Lumbar puncture has been clinically used as an access method for spinal anesthesia and for introduction of therapeutic or diagnosis agents.

An intrathecally administered vector comprising a nucleic acid sequence may therefore be used to direct the expression of any exogenous nucleic acid in neuronal cells located in dorsal root ganglia to provide therapeutic products to peripheral neurons following traumatic injury or disease or to study gene expression in peripheral neurons.

In different embodiments, the vector is a viral vector. "Viral vector" refers to recombinant viruses engineered to effect the introduction of exogenous nucleic acids into cells. Viral vectors include, for example, retroviruses, adenoviruses, adeno-associated viruses (AAV), baculoviruses, vaccinia viruses, herpes viruses, alphavirsus vectors, alphavirus replicons and lentivirus vectors.

The delivery of nucleic acids into a cell by a viral vector may require specific interactions between molecules on the outer surface of the viral envelope and molecules on the cell to be transfected, for example, such as those between the glycoprotein D and the cell surface receptors, herpesvirus entry mediator A, or nectin-1 (Krummenacher et al. 2003, *Journal of Virology* 77(16): 8985). Alternatively, the viral gene delivery system may involve non-specific interactions, for example, such as the baculoviral infection of mammalian cells. Baculoviruses display a broad tropism for mammalian cells and viral entry may be mediated by electrostatic interactions which may not be cell-specific (Sarkis et al. 2000, *Proc. Nat Acad. Sci.* 97:14638). Depending on the nature of the target cell sought to be transfected, a person skilled in the art can readily determine which of the viral gene-delivery systems may be the most appropriate In specific embodiments, the viral vector may be a baculovirus vector or an AAV vector. Baculovirus vectors have recently been viewed as a new generation of gene therapy vehicles, due to their broad tropism in both proliferating and non-proliferating quiescent mammalian cells, the lack of replication in vertebrate cells and little to no microscopically observable cytotoxcity (Ghosh et al., 2002, *Mol Ther* 6:5; Kost & Condreay, 2002, *Trends Biotechnol* 20:173). Baculovirus vectors, such as, for example, those derived from *Autographa Californica* Multicapsid Nucleopolyhedrovirus (AcMNPV), may be well suited for gene therapy of non-dividing cells because they are episomal and their promoters are silent in mammalian cells, making them non replicative in human cells (Sarkis et al. 2000, *Proc. Nat. Acad. Sci.* 97: 14638). Baculovirus vectors have been shown to transfect brain cells when directly injected in vivo (Sarkis et al. 2000, *Proc. Nat. Acad. Sci* 97: 14638; Tani et al. 2003, *Journal of Virology* 77(18):9799). Further, relative to adenoviral vectors, baculovirus vectors may elicit much less of a microglia response (Lehtolainen et al. 2002, *Gene Therapy* 9:1693).

The possibility of using baculovirus vectors for gene transfection in the nervous system has been investigated in two studies. An initial report described the efficient transduction of neural cells in vitro and in vivo (Sarkis et al., 2000, *Proc. Nat. Acad. Sci* 97: 14638). In primary cell cultures of human embryonic brains, neuroepithelial, neuroblastic, and glial cells could be infected, although in vivo studies using adult nude mice demonstrated that mainly astrocytes and only a few neurons were transduced. The second study examined the cell-type specificity of baculovirus-mediated gene expression in the brain and identified cuboidal epithelial cells of the choroids plexus as the main target, with modest gene expression in endothelial cells and very limited or no expression in other types of brain cells, including neurons and astrocytes (Lehtolainen et al., 2002, *Gene Therapy* 9:1693).

The inventors have shown for the first time that baculoviruses are capable of infecting sensory neurons in DRG by intrathecal injection.

A person skilled in the art would readily appreciate how to construct baculoviral vectors for use in the invention. Recombinant baculovirus vectors may be constructed according to instructions accompanying commercial baculovirus expression systems, for example, the Bac-to-Bac® Expression system (Invitrogen). Recombinant baculoviral vectors may be modified by molecular biological techniques, including PCR-based techniques and other cloning techniques, as will be known to a skilled person and described, for example, in Sambrook et al., *Molecular Cloning A Laboratory Manual* ($3^{rd}$ ed.), Cold Spring Harbour Press.

Viral vectors may be engineered to contain increased levels of the viral envelope glycoprotein gp64. Although the mechanism of action of gp64 on viral entry into mammalian cells is unknown, viral vectors with increased levels of pg64 have enhanced levels of transduction (Tani et al. 2001, *Virology* 279: 343). Recombinant viral vectors may also be modified by incorporating foreign envelope proteins into the envelope of the viral virion. For example, increased neural infection efficiency may be achieved by pseudotyping (Sarkis et al. 2000, *Proc. Nat. Acad. Sci.* 97: 14638) rabies virus glycoprotein (RVG) or vesicular stomatitis virus G protein (VSVG) (Tani et al. 2003, *Journal of Virology* 77(18): 9799), herpes envelope glycoprotein or envelope proteins derived from α- or rhabdovirus (Ghosh et al. 2002, *Molecular Therapy* 6(1):5) into the envelope of the viral virion. RVG is known to use the nicotinic acetylcholine receptor and the low affinity nerve growth factor receptor for viral entry, and a RVG-modified baculovirus has been shown to have 10-5000 fold higher efficiency of neural cell transfection than the unmodified baculovirus (Tani et al. 2003, *Journal of Virology* 77(18): 9799). Alternatively, the cell specificity of viral infection may be increased by incorporating antibodies directed against cell-specific protein receptors into the viral envelope.

To minimize or avoid any possibility for inactivation by serum complement (Tani et al. 2003, *Journal of Virology*, 77(18):9799), recombinant viruses may be modified to increase their resistance to the complement system, including, for example, by incorporating human decay-accelerating factor into a viral envelope (Hüser et al., 2001, *Nature Biotechnology* 19:451).

In other embodiments, the vector is a non-viral vector. "Non-viral vectors" refers to systems other than viral vectors that may be used to introduce exogenous nucleic acids, for example plasmids, into a cell. Non-viral vectors include, but are not limited to polymer-based, peptide-based and lipid-based vectors. Many non-viral vectors are commercially available, such as, for instance PEI 25K (Sigma-Aldrich, St. Louis, Mo.) Lipofectamine™ 2000 (Invitrogen, Carlsbad Calif.). Complexes of these vectors and nucleic acids may be prepared according to commercial instructions, or by following protocols known to a person skilled in the art, such as, for example, Boussif et al. (1995, *Proc. Nat. Acad. Sci.* 92:7297).

Generally, non-viral gene-delivery systems rely on the direct delivery of the target nucleic acid or on nonspecific internalization methods. Non-viral gene delivery systems and methods for their transfection would be known to a person skilled in the art, and include, for example, naked plasmids, DEAE-dextran, calcium phosphate co-precipitation, microinjection, liposome-mediated transfection, cationic lipids, and polycationic polymers. As would further be appreciated by a person skilled in the art, some of these methods, such as, for example, microinjection, liposome-mediated transfection, polycationic polymers, are capable of transfecting cells both in vivo and in vitro. These non-viral vectors may be modified to enhance nerve-specific transfection, for example by linking the vector to one or more ligands that may specifically or preferentially bind to neuronal cells. For example, nerve-specific transfection of polylysine/DNA complexes may be obtained by covalently linking the nontoxic fragment C of tetanus toxin to polylysine (Knight et al. 1999, Eur J. Biochem 259: 762-769).

Non-viral vectors containing DNA with bacterial sequences often have increased palindromic CpG sequences relative to eukaryotes, and these foreign CpG sequences may serve as strong immunostimulatory agents in vertebrates. Reducing CpG content therefore may be advantageous and may also enhance protein expression as CpG sequences may be methylated in eukaryotic hosts, which can result in the transcriptional silencing (Chevalier-Mariette et al. 2003, Genome Biology 4:R53). In some embodiments, the CpG content of the DNA of non-viral DNA-based vectors is reduced. Methylation of cytosine residues within a CMV promoter-enhancer (CMV P/E) of a first generation adenovirus, including at CpG sites, has been shown to be the major mechanism for decreased transgene expressions (Brooks et al. 2004, J. Gene Med. 6:395). A person skilled in the art would readily appreciate that the CpG dinucleotide content of a vector may be reduced using standard molecular biology techniques, such as oligonucleotide or PCR-based mutagenesis as described, for example, in Chevalier-Mariette et al. 2003, Genome Biology 4:R53.

In some embodiments, the non-viral vector is a polyethyleneimine/DNA complex (PEI/DNA). Polycationic PEI has a high transfection efficiency both in vitro and in vivo (Boussif et al. 1995, Proc. Nat. Acad. Sci. 92:7297). Preferably, the DNA in PEI/DNA is plasmid DNA. In PEI/DNA complexes, the ratio of PEI nitrogen to DNA phosphate is preferably 6 to 30, more preferably 6 to 20 and most preferably 6 to 15 (Boussif et al. 1995, Proc. Nat. Acad. Sci. 92:7297). A person skilled in the art can readily prepare PEI/DNA, for example, by following established commercial protocols. Once in the nervous system, PEI may mediate DNA transfection in terminally differentiated non-dividing neurons (Boussif et al. 1995, Proc. Nat. Acad. Sci. 92:7297). After direct brain injection, PEI/DNA complexes can provide transgene expression levels higher than those obtained with HIV-derived vectors and within the same range as that achieved with adenoviral vectors. The PEI in a PEI/DNA complex may have an average molecular weight of 800 kD, 50 kD, or more preferably 25 kD (Abdallah et al. 1996, Hum Gene Ther. 7(16):1947). PEI may also be covalently modified with other polymers, such as for example polyethylene glycol to reduce the cytotoxicity of the PEI/DNA complex. (Shi et al. 2003, Gene Therapy 10, 1179).

In different embodiments, the vector comprises a promoter operably linked to a coding nucleic acid sequence. The promoter may be a strong viral promoter such as CMV or a neuronal-specific promoter. Specific gene expression in a selected cell type can be achieved by using a cell-specific promoter.

Neuron-specific promoters may be any nucleotide sequence that functions to activate transcription of operably linked sequences within neurons or neuronal cells and substantially not in other cells types. A promoter does not substantially activate transcription if the levels of transcription of operably linked sequences in any of those cell types are sufficiently low so as not to affect the physiological functioning of the cell.

Neuron-specific promoters may include promoters for neuronal genes such as Synapsin I, Neuron-specific enolase, Neurofilament-L and Neuropeptide Y and promoters specific for particular types of neuronal cells. For example, tyrosine hydroxylase gene promoter (4.8 kb 5' UTR) is specific for catecholaminergic and the CNS neurons, dopamine-b-hydroxylase gene promoter is specific for adrenergic and noradrenegic neurons and L7 Purkinje cell protein promoter is specific for retinal rod bipolar neurons. For these and other neuron-specific promoters including, D1A dopamine receptor gene promoter, human hypoxanthine phosphoribosyltransferase promoter, SCG10 promoter, Tα1 α-tubulin promoter, aldolase C promoter, beta-tubulin gene promoter, GnRH gene enhancer and promoter, glutamate decarboxylase 65 gene promoter, beta-galactoside alpha1,2-fucosyltransferase gene promoter, neuronal nicotinic acetylcholine receptor beta3 gene promoter, GABA(A) receptor delta subunit gene promoter, neuron-specific FE65 gene promoter, N-type calcium channel alpha1B subunit gene promoter and microtubule-associated protein 1B gene promoters, see Harrington C A, Lewis E J, Krzemien D, Chikaraishi D M. Identification and cell type specificity of the tyrosine hydroxylase gene promoter. Nucleic Acids Res 1987, 15:2363-2384; Coker G T 3rd, Vinnedge L, O'Malley K L; Characterization of rat and human tyrosine hydroxylase genes: functional expression of both promoters in neuronal and non-neuronal cell types. Biochem Biophys Res Commun 1988, 157:1341-1347; Banerjee S A, Hoppe P, Brilliant M, Chikaraishi D M. 5' flanking sequences of the rat tyrosine hydroxylase gene target accurate tissue-specific, developmental, and transsynaptic expression in transgenic mice. J Neurosci 1992, 12:4460-4467; Morita S, Kobayashi K, Mizuguchi T, Yamada K, Nagatsu I, Titani K, Fujita K, Hidaka H, Nagatsu T. The 5'-flanking region of the human dopamine beta-hydroxylase gene promotes neuron subtype-specific gene expression in the central nervous system of transgenic mice. Brain Res Mol Brain Res 1993; 17:239-244; Ishiguro H, Kim K T, Joh T H, Kim K S. Neuron-specific expression of the human dopamine beta-hydroxylase gene requires both the cAMP-response element and a silencer region. J Biol Chem 1993; 268:17987-17994; Hoyle G W, Mercer E H, Palmiter R D, Brinster R L. Cell-specific expression from the human dopamine beta-hydroxylase promoter in transgenic mice is controlled via a combination of positive and negative regulatory elements. J Neurosci 1994, 14:2455-2463; Severynse D M, Colapietro A M, Box T L, Caron M G. The human D1A dopamine receptor gene promoter directs expression of a reporter gene to the central nervous system in transgenic mice. Brain Res Mol Brain Res 1995, 30:336-346; Mouradian M M, Minowa M T, Minowa T. Promoter structure of the human gene coding for the D1A dopamine receptor. Adv Neurol 1993, 60:343-345; Stout J T, Chen H Y, Brennand J, Caskey C T, Brinster R L. Expression of human HPRT in the central nervous system of transgenic mice. Nature 1985; 317:250-252; Rincon-Limas D E, Geske R S, Xue J J, Hsu C Y, Overbeek P A, Patel P I. 5'-flanking sequences of the human HPRT gene direct neuronal expression in the brain of transgenic mice. J Neurosci Res 1994; 38:259-267; Schwartz M L, Bruce J, Shneidman P S, Schlaepfer W W. Deletion of 3'-untranslated region alters the level of mRNA expression of a neurofilament light subunit transgene. J Biol Chem 1995; 270:26364-9; Forss-Petter S, Danielson P E, Catsicas S, Battenberg E, Price J, Nerenberg M, Sutcliffe J G. Transgenic mice expressing beta-galactosidase in mature neurons under neuron-specific enolase promoter control. Neuron 1990; 5:187-197; Twyman R M, Jones E A. Sequences in the proximal 5' flanking region of the rat neuron-specific enolase (NSE) gene are sufficient for cell type-specific reporter gene expression. J Mol Neurosci 1997; 8:63-73; Andersen J K, Garber D A, Meaney C A, Breakefield X O. Gene transfer into mammalian central nervous system using herpes virus vectors: extended expression of bacterial lacZ in neurons using the neuron-specific enolase promoter. Hum Gene Ther 1992; 3:487-499; Wuenschell C W, Mori N, Anderson D J. Analysis of SCG10 gene expression in transgenic mice reveals that neural specificity is achieved through selective derepression. Neuron 1990; 4:595-602; Mori N, Stein R, Sigmund O, Anderson D J. A cell type-preferred silencer element that controls the neural-specific expression of the SCG10 gene. Neuron 1990; 4:583-594; Hoesche C, Sauerwald A, Veh R W, Krippl B, Kilimann M W. The 5'-flanking region of the rat synapsin I gene directs neuron-specific and developmentally regulated reporter gene expression in transgenic mice. J Biol Chem 1993; 268:26494-26502; Kilic E, Hermann D M, Kugler S, Kilic U, Holzmuller H, Schmeer C, Bahr M. Adenovirus-mediated Bcl-X(L) expression using a neuron-specific synapsin-1 promoter protects against disseminated neuronal injury and brain infarction following focal cerebral ischemia in mice. Neurobiol Dis 2002; 11:275-284; Gloster A, Wu W, Speelman A, Weiss S, Causing C, Pozniak C, Reynolds B, Chang E, Toma J G, Miller F D. The T alpha 1 alpha-tubulin promoter specifies gene expression as a function of neuronal growth and regeneration in transgenic mice. J Neurosci 1994; 14:7319-7330; Thomas M, Makeh I, Briand P, Kahn A, Skala H. Determinants of the brain-specific expression of the rat aldolase C gene: ex vivo and in vivo analysis. Eur J Biochem 1993; 218:143-151; Thomas M, Skala H, Kahn A, Tuy F P. Functional dissection of the brain-specific rat aldolase C gene promoter in transgenic mice. Essential role of two GC-rich boxes and an HNF3 binding site. J Biol Chem 1995; 270: 20316-20321; Dennis K, Uittenbogaard M, Chiaramello A, Moody S A. Cloning and characterization of the 5'-flanking region of the rat neuron-specific Class III beta-tubulin gene. Gene 2002 294:269-277; Waldbieser G C, Minth C D, Chrisman C L, Dixon J E. Tissue-specific expression of the human neuropeptide Y gene in transgenic mice. Brain Res Mol Brain Res 1992; 14:87-93; Lawson M A, Macconell L A, Kim J, Powl B T, Nelson S B, Mellon P L. Neuron-specific expression in vivo by defined transcription regulatory elements of the GnRH gene. Endocrinology 2002; 143:1404-1412; Wolfe A, Kim H H, Tobet S, Stafford D E, Radovick S. Identification of a discrete promoter region of the human GnRH gene that is sufficient for directing neuron-specific expression: a role for POU homeodomain transcription factors. Mol Endocrinol 2002; 16:435-449; Makinae K, Kobayashi T, Kobayashi T, Shinkawa H, Sakagami H, Kondo H, Tashiro F, Miyazaki J, Obata K, Tamura S, Yanagawa Y. Structure of the mouse glutamate decarboxylase 65 gene and its promoter: preferential expression of its promoter in the GABAergic neurons of transgenic mice. J Neurochem 2000; 75:1429-14371; Hitoshi S, Kusunoki S, Kanazawa I, Tsuji S. Dorsal root ganglia neuron-specific promoter activity of the rabbit beta-galactoside alpha1,2-fucosyltransferase gene. J Biol Chem 1999; 274:389-396; Roztocil T, Matter-Sadzinski L, Gomez M, Ballivet M, Matter J M. Functional properties of the neuronal nicotinic acetylcholine receptor beta3 promoter in the developing central nervous system. J Biol Chem 1998; 273:15131-15137; Luscher B, Hauselmann R, Leitgeb S, Rulicke T, Fritschy J M. Neuronal subtype-specific expression directed by the GABA(A) receptor delta subunit gene promoter/upstream region in transgenic mice and in cultured cells. Brain Res Mol Brain Res 1997; 51:197-211; Zambrano N, De Renzis S, Minopoli. G, Faraonio R, Donini V, Scaloni A, Cimino F, Russo T. DNA-binding protein Pur alpha and transcription factor YY1 function as transcription activators of the neuron-specific FE65 gene promoter. Biochem J 1997; 328:293-300; Kim D S, Jung H H, Park S H, Chin H. Isolation and characterization of the 5'-upstream region of the human N-type calcium channel alpha1B subunit gene. Chromosomal localization and promoter analysis. J Biol Chem 1997; 272:5098-5104 and Liu D, Fischer I. Two alternative promoters direct neuron-specific expression of the rat microtubule-associated protein 1B gene. J Neurosci 1996; 16:5026-5036. Other neuron-specific promoters will be known to persons skilled in the art.

A neuron-specific promoter comprises at least one nucleotide sequence capable of activating neuronal cell specific expression of operably linked sequences and in some embodiments the nucleotide sequence will retain the minimum binding site(s) for transcription factor(s) required for the sequence to act as a promoter. In some embodiments, the vector comprises multiple copies of the same sequence or two or more different nucleotide sequences each of which is effective to activate transcriptional activity. For various promoters which may be used, transcription factor binding sites may be known or identified by one of ordinary skill using methods known in the art as described above. Suitable promoter/enhancer constructs may be readily determined by standard expression assays.

Platelet-derived growth factor β-chain (PDGF β) promoter (Sasahara M, Fries J W, Raines E W, Gown A M, Westrum L E, Frosch M P, Bonthron D T, Ross R, Collins T. PDGF β-chain in neurons of the central nervous system, posterior pituitary, and in a transgenic model. Cell 1991; 64:217-227) has been shown to be specific for neuronal cells, including dopaminergic neurons and in one embodiment, the neuron-specific promoter is PDGF β promoter. In a specific embodiment, the neuron-specific promoter is human PDGF β promoter.

The transcriptional activity of a promoter in some instances may be weak, providing a less than ideal level of expression of therapeutic gene sequences. In various embodiments, the promoter may be operably linked to an enhancer. As would be understood by a skilled person, an "enhancer" is any nucleotide sequence capable of increasing the transcriptional activity of an operably linked promoter and, in the case of a neuron-specific promoter, of selectively increasing the transcriptional activity of the promoter in neuronal cells. A number of enhancers are known and a person skilled in the art would also know how to screen for novel enhancer sequences, for instance, by screening nucleotide sequences capable of increasing the transcription of a reporter gene, for instance, through functional mapping.

A first nucleic acid sequence is operably linked with a second nucleic acid sequence when the sequences are placed in a functional relationship. For example, a coding sequence is operably linked to a promoter if the promoter activates the transcription of the coding sequence. Similarly, a promoter and an enhancer are operably linked when the enhancer increases the transcription of operably linked sequences. Enhancers may function when separated from promoters and as such, an enhancer may be operably linked to a promoter even though it is not contiguous to the promoter. Generally, however, operably linked sequences are contiguous.

In different embodiments, the enhancer may be a heterologous enhancer, meaning a nucleotide sequence which is not naturally operably linked to a promoter and which, when so operably linked, increases the transcriptional activity of the promoter. Reference to increasing the transcriptional activity is meant to refer to any detectable increase in the level of transcription of an operably linked sequence compared to the level of the transcription observed with a promoter alone, as may be detected in standard transcriptional assays, including those using a reporter gene construct.

The enhancer may be a known strong viral enhancer element such as Rous sarcoma virus (RSV) promoter (Gorman et al 1982. *Proc. Nat. Acad. Sci.* 79:6777-6781), SV40 promoter (Ghosh et al. 1981, *Proc. Nat. Acad. Sci.* 78:100), CMV enhancer or promoter including CMV immediate early (IE) gene enhancer (CMVIE enhancer) (Boshart et al 1985, *Cell* 41:521; Niwa et al. 1991, *Gene* 108:193; see also U.S. Pat. Nos. 5,849,522 and 5,168,062).

In one embodiment of the present invention, a CMV enhancer is operably linked upstream to PDGF β promoter. In a further embodiment, CMVE enhancer is operably linked upstream to PDGF β promoter and the two sequences are contiguous. In another embodiment, a CMV enhancer is operably linked to a CMV promoter (CMV E/P).

Further examples of neuron-specific promoters that may be operably linked to enhancers, including allelic variants and derivatives of known promoter and enhancer sequences, are described in U.S. application Ser. No. 10/407,009.

In various embodiments, such variants and derivatives may be substantially homologous in that they hybridize to the known enhancer and promoter sequences under moderate or stringent conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH. Stringent hybridization may, for example, be conducted in 5×SSC and 50% formamide at 42° C. and washed in a wash buffer consisting of 0.1×SSC at 65° C. Washes for stringent hybridization may, for example, be of at least 15 minutes, 30 minutes, 45 minutes, 60 minutes, 75 minutes, 90 minutes, 105 minutes or 120 minutes.

The degree of homology between sequences may also be expressed as a percentage of identity when the sequences are optimally aligned, meaning the occurrence of exact matches between the sequences. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). In various embodiments, the variants and derivatives may be at least 50%, at least 80%, at least 90% or at least 95% identical as determined using such algorithms.

In different embodiments, the vector comprises a gene encoding a marker protein whose expression and cellular or subcellular localization maybe readily determined. "Marker protein" refers to a protein whose presence or subcellular localization may be readily determined, such as a green fluorescent protein (GFP) or any of its enhanced derivatives. Other marker proteins would be known to a person skilled in the art. In different embodiments, the gene may encode an enzyme whose expression may be readily determined by providing a specific substrate and detecting the products of enzymatic turnover, such as, for example, by providing luciferin to cell or cell lysates containing luciferase. In other embodiments, the marker protein may be any protein whose expression may be detected immunologically, for example by providing a labeled antibody that specifically recognizes the marker protein. The antibody is preferably a monoclonal antibody and may be directly or indirectly labeled according to methods known in the art, such as, for example, labeling with a fluorescent dye and detecting expression of the protein by fluorescence microscopy. Other immunological detection methods, including without limitation, immunogold staining, radiolabelling, colourometric enzymatic precipitation would be known to a person skilled in the art.

Preferably, the nucleic acid vector comprises a therapeutic gene or a therapeutic transgene whose expression produces a therapeutic product. The term "gene" is used in accordance with its usual definition, to mean an operatively linked group of nucleic acid sequences. As used herein, "therapeutic product" describes any product that effects a desired result, for example, treatment, prevention or amelioration of a disease. The therapeutic product may be a therapeutic protein, a therapeutic peptide or a therapeutic RNA, such as, for example, a small interfering RNA (siRNA) or an anti-sense RNA.

In some embodiments, the therapeutic product is a neurotrophic factor, such as, for example a nerve growth factor. As used herein, "nerve growth factor" refers to any factor that can promote nerve cell growth and/or nerve regeneration such as, for example, neurotrophins, neurotrophin receptors and neurotrophic factors. "Neurotrophin" refers to a protein family that can support neuronal survival and/or nerve regeneration. Neurotrophins include, for example, Nerve Growth Factor (NGF), brain-derived neurotrophic factor (BDNF), neurotrophin 3 (NT-3), neurotrophin 4/5 (NT-4/5) as well as neurotrophin variants. A "variant" refers to a protein whose sequence differs from that of the naturally occurring protein by one or more amino acid substitutions, additions or deletions but maintains some of the biological activity of the naturally occurring protein. As will be appreciated by a person skilled in the art, a variant may possess about 60%, 70%, 80% preferably 90%, or more preferably greater than 95% homology with a naturally occurring protein. In specific embodiments, the therapeutic product is NGF. In a specific embodiment, the vector comprises a gene encoding NGF operatively coupled to CMV E/P.

"Neurotrophin receptor" refers to proteins that are able to bind neurotrophins. Neurotrophin receptors include, for example, the low-affinity p75 receptors and high-affinity receptors such as, for example, trkA, trkB, and trkC and their variants. "Neurotrophic factors" include, for example, ciliary neurotrophic factor (CNTF), hippocampus-derived neurotrophic factor (HDNF), leukemia inhibitory factor (LIF) (Yamamori et al. 1989, *Science* 246: 1412), acidic and basic fibroblast growth factor (aFGF, bFGF) and their variants.

"Neurotrophic factors" also include other factors that may enhance neurite outgrowth in vitro and/or in vivo, that may potentiate axonal regeneration, or that may be effective in counteracting the negative effects of chronic axotomy on axonal regeneration, such as, for example, the immunophillin ligand FK506 (Lee et al. 2000, *Muscle Nerve* 23:633) and its variants.

In other embodiments, the therapeutic product is an anti-apoptotic factor such as, for example, bcl-2 or bcl-XL. In adults, peripheral nerve damage is followed by 20 to 40% cell loss in DRG, which is likely from apoptosis (Terenghi 1999, *J. Anat.* 194:1). Without being limited to any particular theory, it is believed that the delivery of anti-apoptotic proteins to neuronal cells in the DRG may reduce or may prevent this cell loss.

Methods for preparing recombinant vectors would be well-known to a person skilled in the art, for example, those described in Sambrook et al. Molecular Cloning, A Laboratory Manual ($3^{rd}$ ed) Cold Spring Harbour Laboratory Press (2001) and other laboratory manuals, and as described in commercial instructions.

To aid in administration, the vectors may be formulated as an ingredient in a pharmaceutical composition. The compositions may routinely contain pharmaceutically acceptable concentrations of salt, buffering agents, preservatives and various compatible carriers or diluents. For all forms of delivery, the vectors may be formulated in a physiological salt solution.

The proportion and identity of the pharmaceutically acceptable diluent is determined by chosen route of administration, compatibility with the vector and standard pharmaceutical practice. Generally, the pharmaceutical composition will be formulated with components that will not significantly impair the biological activities of the vector. Suitable vehicles and diluents are described, for example, in Remington's Pharmaceutical Sciences (Remington's Pharmaceutical Sciences, Mack Publishing Company, Easton, Pa., USA 1985).

Solutions of the vectors may be prepared in a physiologically suitable buffer. Under ordinary conditions of storage and use, these preparations contain a preservative to prevent the growth of microorganisms, but that will not inactivate the vector. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999.

In some embodiments, the vectors are administered to a vertebrate host. In a specific embodiment, the vectors are administered to a human host.

DRG have been considered as early and critical targets in several types of peripheral neuropathies, including diabetic neuropathy, the most prevalent form of peripheral neuropathies (Kishi et al 2002, *Diabetes* 51:819; England & Asbury, 2004 *Lancet* 363:2151). Patients with diabetic neuropathy may display exclusive sensory and autonomic symptoms without obvious motor disorder. Pathological studies of human and experimental diabetic neuropathies have confirmed cell loss in DRG, which may have resulted from the observed loss of mylenated fibers and axonal atrophy. Neurons in DRG are also directly involved in the pathophysiology of peripheral nerve injuries caused by physical trauma, compression or transection. Peripheral nerve transection may also cause biochemical alterations in the expression of neuropeptides, cytokines and transcription factors in the perikaryon of the surviving neurons in the affected DRGs and atrophy in the proximal nerve stump (Stoll & Muller 1999, *Brain Pathol.* 9(2):313). These pathological alterations will certainly disturb the transmission of sensory signals from body parts like the skin, muscles and internal organs to the CNS. As a result, parts of the body may function inappropriately or not at all.

Expression of therapeutic genes, especially those encoding neurotrophins, in DRG prevents nerve degeneration in experimental neuropathy (Glorioso et al. 2003, *Curr Opin Mol Ther.* 5:483). However, gene transfer to DRG is still challenging due to their anatomic features. In previous studies, the transfer was achieved through intramuscular or subcutaneous injection of viral vectors, mainly herpes simplex virus (HSV), that can be taken up by nerve terminals and then transported in axoplasm to somas of neurons in DRG (Haase et al., 1998, *J. Neurol Sci.*160 Suppl.; Jackson et al., 2003, *Virology* 314:45; Goss et al. 2001, *Gene Therapy* 8:551). While being effective, this approach relies on functioning cellular mechanisms including endocytosis at nerve terminals and retrograde axonal transport, which may already be damaged under peripheral neuropathic conditions.

In another method not dependent on nerve terminal endocytosis and retrograde axonal transport, Glatzel et al. (2000, *Proc. Nat. Acad. Sci.* 97:442) and Xu et al. (2003, *Biomaterials* 24:2405) have recently used a microneurosurgical technique for direct injection of gene transfer vectors into DRG, that resulted in strong expression of reporter genes along sensory neural pathways. The injection procedure requires removing a piece of vertebra to gain access to DRG. It is also invasive to the tissues of DRG and not practical when a repeat injection scheme is required, such as, for example, for the long-term therapy of a chronic disorder.

The minimally invasive delivery of vectors comprising genes encoding therapeutic products to the cell bodies of neurons within dorsal root ganglia according to the invention therefore may be advantageously used for treating peripheral neuropathies to promote the growth and/or regenerate injured peripheral nerves. "Peripheral neuropathy", as will be understood by a person skilled in the art, refers to the loss of peripheral neuronal cells or their function with or without obvious motor disorder. Such cells are therefore target cells that are affected by a peripheral neuropathy and that may be treated by expression of therapeutic gene within the cells. Peripheral neuropathies may be caused by a disease or disorder or as the result of systemic illnesses. Many neuropathies have well-defined causes such as, for example, diabetes, uremia, AIDS, Lyme disease or nutritional deficiencies. Other causes of peripheral neuropathy include mechanical pressure such as compression or entrapment, direct trauma, penetrating injuries, contusions, fracture or dislocated bones; pressure involving the superficial nerves; intraneural hemorrhage; exposure to cold or radiation or, rarely, certain medicines or toxic substances; and vascular or collagen disorders such as, for example, atherosclerosis, systemic lupus erythematosus, scleroderma, sarcoidosis, rheumatoid arthritis, and polyarteritis nodosa. Although the causes of peripheral neuropathy are diverse, they generally produce common symptoms including weakness, numbness, paresthesia (abnormal sensations such as burning, tickling, pricking or tingling) and pain in the arms, hands, legs and/or feet. A large number of cases are of unknown cause.

The vectors are administered preferably by intrathecal injection in an amount sufficient to achieve the desired result, for example, expression of therapeutic gene in an effective amount in the target cells.

In some embodiments, the vector is administered by lumbar puncture. Lumbar puncture is a relatively routine and non-traumatic clinical procedure that poses minimal risk to the spinal chord. Generally, a solution comprising the vector is administered into the cerebrospinal fluid with a narrow needle, such as, for example a 26 gauge needle, connected to a syringe or microsyringe. In rats, the proper intrathecal location of the needle may be confirmed by a slight tail movement, indicating the proper injection into the subarachnoid space. After injection, the needle may remain in the intrathecal space for a period of time, such as, for example, 2 minutes before being removed.

Effective amounts of vectors can be given repeatedly, depending upon the effect of the initial treatment regimen. Administrations are typically given periodically, while monitoring any response. It will be recognized by a skilled person that lower or higher dosages may be given, according to the administration schedules and routes selected.

When administered to a human patient, for example, the vectors are administered in an effective amount and for a sufficient time period to achieve a desired result. For example, the vectors may be administered in quantities and dosages necessary to deliver a therapeutic gene, the product of which functions to alleviate, improve, mitigate, ameliorate, stabilize, prevent the spread of, slow or delay the progression of or cure a peripheral neuronal neuropathy.

The effective amount to be administered to a patient can vary depending on many factors such as, among other things, the pharmacodynamic properties of the therapeutic gene product, the mode of administration, the age, health and weight of the subject, the nature and extent of the disorder or disease state, the frequency of the treatment and the type of concurrent treatment, if any. In embodiments employing viral vectors, the effective amount may also depend on the virulence and titre of the virus.

One of skill in the art can determine the appropriate amount based on the above factors. Vectors may be administered initially in a suitable amount that may be adjusted as required, depending on the clinical response of the patient. The effective amount of a vector can be determined empirically and depends on the maximal amount of the vector that can be safely administered. In some embodiments, the vector may have little cytotoxicity in vertebrates and may be administered in large amounts. However, the amount of vectors administered should be the minimal amount that produces the desired result.

In various embodiments, a dose of about $10^9$ recombinant baculovirus particles are administered to a human patient. In other embodiments, about $10^2$ to about $10^9$ recombinant baculovirus particles, about $10^6$ to about $10^9$ recombinant baculovirus particles, about $10^2$ to about $10^7$ recombinant baculovirus particles, about $10^3$ to about $10^6$ recombinant baculovirus particles, or about $10^4$ to about $10^5$ recombinant baculovirus particles may be administered in a single dose. In some embodiments, the vector may be administered more than once, for example, by repeated injections. In other embodiments, the viral vector may be repeatedly administered though an intrathecal catheter connected to a reservoir containing a composition comprising the vector, as described in (Jackson et al. 2001, *Human Gene Therapy* 12: 1827).

In other embodiments, a non-viral vector comprising about 4 µg of DNA may be administered to a host in a single dose. Non-viral vectors may only transiently express a therapeutic gene once transfected into target cells, resulting in less than optimal transgene expression. In some embodiments of the invention, the vector may be administered more than once, for example, by repeated injection. In other embodiments, the non-viral vector may be repeatedly administered though an intrathecal catheter connected to a reservoir containing a composition comprising the vector, as described in Jackson et al. 2001, *Human Gene Therapy* 12: 1827).

Transected peripheral nerves may advantageously be treated as follows. The vector encoding a therapeutic gene product, for example, a nerve growth factor such as NGF, is intrathecally administered to DRG neuronal cells of a host whose transected distal and proximal nerve stumps have been secured to a nerve guide conduit. The vector may be administered into the cerebrospinal fluid surrounding a dorsal root ganglion to deliver the nucleic acid into the cell body of the transected nerve. For example, if the sciatic nerve is transected, the vector may be intrathecally injected by lumbar injection into the cerebrospinal fluid in an intraspine space between the L4 and L5 vertebrae.

As used herein, "nerve guide conduit" also known as a "nerve guidance channel" or simply "nerve guide" refers to a device with a first and second open end connected by an internal passage, wherein the internal diameter of the conduit is sufficient to accept sections at both ends. Nerve guide conduits may serve to direct axons sprouting from the proximal nerve end, may provide a conduit for the diffusion of growth factors secreted by the injured nerve ends, and may reduce the infiltration of scar tissue (Schmidt et al. 2003, *Annu Rev Biomed Eng* 5: 293). As is known in the art, the nerve guide conduit may be derived from biomaterials, such as extracellular matrix proteins, for example collagen (U.S. Pat. No. 50,190,987), laminin, fibronectin, fibrin/fibrinogen, hyaluronic acid-bases materials or from materials such as, for example silicon, expanded poly(tetrafluoroethylene). Synthetic nerve guide conduits may also be made of biosorbable or biodegradable materials, for example, such as poly(lactic acid) (PLA), poly(glycolic acid) (PLG), poly(lactic-co-glycolic acid) (PLGA), poly(caprolactone), poly(urethane), poly(organo)phosphazene, poly(3-hydroxybutyrate) and methacrylate-based hydrogels. (See Schmidt & Leach and reference therein). The nerve guide conduit may be non-porous, porous or semi-porous, may incorporate neuron support cells, such as, for example, Schwann cells, and may have an oriented nerve substratum and may have one or more intraluminal channels (Hudson et al. 1999, *Clin Plast Surg* 26:617).

A person skilled in the art would know how to secure a transected nerve into a nerve guide conduit, for example, following Schmidt et al. 2003, *Ann. Rev. Biomed. Eng.* 293. Generally, the proximal and distal stumps of a transected peripheral nerve are secured within an internal channel of a nerve guide conduit by, for example, 9-0 or 10-0 sutures. Preferably, the internal channel of the nerve guide conduit is filled with a solution, suspension or gel supportive of axonal outgrowth.

In normal circumstances, NGF is present very low concentrations, and rapidly increases upon nerve injury in an animal model. Upon transection, NGF is produced mainly by the target tissue and Schwann cells in the distal stump of the damaged nerves, and its retrogradely transported to the nerve cell body. The exogenous expression of NGF within the cell body of neurons in a dorsal root ganglion may supplement or substitute NGF delivered by retrograde transport. Without being limited to any particular theory, the exogenous expression of NGF may promote the anterograde transport of neurotrophic factors to the proximal stump of the transected nerve, and these factors may diffuse though the nerve guide conduit and promote nerve regeneration within the conduit.

As would be understood by a person skilled in the art, the administration of the vector may be accomplished before, or more preferably after, the nerve stumps are secured into the conduit. The timing of the administration of the vector to the host effective to promote peripheral nerve regeneration can be readily determined by the skilled person.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

The word "comprising" is used as an open-ended term, substantially equivalent to the phrase "including, but not limited to". Singular articles such as "a" and "the" in the specification incorporate, unless the context dictates otherwise, both the singular and the plural.

The following examples are illustrative of various aspects of the invention, and do not limit the broad aspects of the invention as disclosed herein.

EXAMPLES

Material and Methods
Gene Delivery Vectors

Three non-viral gene delivery systems, polyethyleneimine (PEI)/plasmid DNA complexes, lipofectamine™ 2000/DNA complexes and a peptide-based system, and two viral vectors, recombinant baculovirus and adeno-associated virus Type 2 (AAV-2) vectors, were tested To prepare PEI/DNA complexes, plasmid DNA pCMV E/P-luc (Liu et al. 2004, *Gene Ther.* 11:52) or pcDNA3.1/NGF was mixed with PEI (25 kDa; Sigma-Aldrich, San Diego, Calif.) in a 5% glucose solution by adding an appropriate amount of a PEI solution into a DNA solution, briefly mixing by vortexing and waiting for 30 min at room temperature. pcDNA3.1/NGF was constructed by inserting a full length DNA fragment obtained from a mouse brain cDNA library into EcoR1 digested pcDNA3 (Invitrogen). Ratios of PEI to DNA used for cell transfection and animal experiments were 10 and 14 equivalents of PEI nitrogen per DNA phosphate, respectively. In some experiments, PEI was labeled with the carbocyanine dyes Cy3 (Amersham, Uppsala, Sweden) before being mixed with DNA. The required amount of the plasmid was calculated by taking into account that 1 µg of DNA contains 3 nmol of phosphate. To prepare lipofectamine™ 2000/DNA complexes, pCMV E/P-luc was mixed with lipofectamine™ 2000 (Invitrogen, Singapore) in a 5% glucose solution by adding the appropriate amount of lipofectamine™ 2000 into the diluted DNA solution, gently mixing and incubating for 20 min at room temperature. Ratios of DNA (in µg) to lipofectamine™ 2000 (in µl) used for animal experiments were 1 to 3.

To prepare a peptide-based gene delivery system, the peptide NL4-10K and PEI600 were used. The peptide contains a 29-amino acid fragment derived from NGF loop 4-containing region (aa80-108) linked with 10-lysine residue as a DNA binding domain (Zeng et al., *J Gene Medicine*, 2004, in press). To prepare DNA complexes, DNA was first complexed with PEI600 at a nitrogen/phosphate ratio of 5 and the peptide was added afterward at a peptide/DNA (nmol/g) ratio of 1.5.

Recombinant baculovirus vectors were constructed according to the manual of Bac-To-Bac® Baculovirus Expression system (Gibco BRL, Life Technologies, USA). Luciferase cDNA under control of the human CMV E/P promoter or a CMV E/PDGF promoter was from vectors constructed in Liu et al. (*Gene Therapy*, 2004, 11: 52). The promoter was inserted between NotI and XbaI sites of pFastBac1 and the luciferase cDNA was between XhoI and HindIII sites downstream of the promoter. Recombinant baculorviruses were propagated in Sf9 insect cells. Budded viruses from insect cell culture medium were filtered through a 0.2-µm pore size filter and concentrated by ultracentrifugation at 25,000 g for 60 min. For uptake experiments, baculoviruses were labeled with the carbocyanine dye Cy3 according to the manual provided by the supplier (Amersham, Uppsala, Sweden). Recombinant AAV-2 vectors were constructed by subcloning, the CMV E/P promoter from pCMV E/P vector or the CMV E/PDGF promoter from pCMV E/PDGF vector (Liu et al. 2004, *Gene Therapy*, 11: 52) into a modified pAAV plasmid that is flanked by the ITR sequences. This pAAV plasmid, named as pAAV-MCS-luc, was constructed by replacing the original sequence between the two Not I sites of plasmid pAAV-MCS (Stratagene, La Jolla, Calif.) by a multiple cloning site (MCS)-luciferase-polyA expression cassette that was PCR amplified from pGL3-basic plasmid (Promega, USA) with forward primer, 5-ATTGCGGC-CGCGGTACCGAGCTCTTACG [SEQ ID NO:1] and reverse primer, 5-ATTGCGGCCGCTTATCGATTTTAC-CACATTTG [SEQ ID NO:2]. The promoter was inserted into pAAV-MCS-luc between the Kpn I and Hind III sites. The plasmid was used, together with AAV-2 packaging plasmid pAAV-RC and adenovirus helper plasmid pHelper (Stratagene, La Jolla, Calif.), to transfect HEK293 (human embryonic kidney) cells. AAV-2 vectors that had been packaged in the transfected HEK293 cells were released from collected cells by two rounds of freeze/thaw cycles and purified by a single-step gravity-flow heparin affinity column.

Animals and Operations

Adult male Wistar rats, weighing 250-320 g and supplied by the Laboratory Animal Center, National University of Singapore, were used throughout the study. For luciferase activity assays, 50 rats were used, among which 30 rats in the time course study (5 per each time interval), 5 each to test PEI, lipofectamine™ 2000, AAV and baculovirus vectors. For immunohistochemical study, 12 rats were used, 6 of which in the sham operated group and 6 in the experimental group. For PCR analysis, 12 rats were used, 6 of which in the sham operated group and 6 in the experimental group. Rats were randomly assigned to each group at various times after injection. They were kept 4 per cage in a light-dark cycle (12 h/12 h) at a constant temperature of 22° C. and at 60% humidity, and fed with normal laboratory rat food. In the handling and care of all animals, the International Guiding Principles for Animal Research as stipulated by World Health Organization (1985) and as adopted by the Laboratory Animal Center, National University of Singapore, were followed.

For intrathecal injection, rats were anaesthetized by an intraperitoneal injection of sodium pentobarbital (60 mg/kg of body weight). The back skin of rats was incised and the spinal column was exposed. The intraspine space between lumbar vertebrae 4 and 5 (L4-5) was chosen as the injection site. A 10 µl micro-syringe connected with a 26-gauge needle was used to perform the injection. The slight movement of rat tails indicated the proper injection into the subarachnoid space. Complexes with 4 µg of plasmid DNA, 1×10$^8$ particles of the AAV-2, or 1×10$^7$ particles of baculovirus in 20 µl were used for each injection. After a slow administration over 2-5 min, the needle was allowed to remain in situ for 2 min before being removed. The skin was closed with surgical clips after the injection.

To produce a rat model for nerve injury and regeneration (Xu et al. 2003, *Biomaterials* 24:2504), right sciatic nerves of anesthetized rats were exposed through a 2 cm long skin incision. A 7 mm piece of the nerve was removed and then the proximal and distal nerve stumps were pulled 2 mm into each opening of a silicone nerve guide conduit (NGC, Tygon® ID: 0.05 inch, OD: 0.09 inch, length: 1.4 cm), leaving a 10 mm interstump gap. Twenty-five micro liter of saline was filled into the tube before the proximal stump was pulled into the tube opening. The two stumps were fixed to the tubes with a single 10/0 perineurial suture (Ethilon). The intrathecal injection into the intraspinearea between L4 and L5 vertebrae of 20 µl of PEI complexes containing 4 µg of pcDNA/NGF, or PEI/pcDNA3/luc complexes for control rats, was carried on immediately after NGC implantation Thirty rats were used in this experiment, 15 of which received the injection of PEI/pcDNA3.1/NGF complexes and the other 15 rats as controls.

Reporter Gene Detection

PCR amplification was carried out to detect transported reporter genes in DRG. 2 days after lumbar intrathecal injection of PEI/DNA complexes or baculovirus vectors, rats were sacrificed by intracardiac perfusion with 0.1 M PBS (pH 7.4) following deep anesthesia and three pairs of companion DRGs (lumbar L4 to L6) around the injection site were collected. The tissues were homogenized by mincing with a razor blade and DNA was extracted according to the standard protocol of a DNeasy Tissue Kit (Qiagen, Hilden, Germany). Oligonucleotide primers for PCR were designed based on the luciferase gene sequence and are listed below: 5' primer, 5'-AT TGC TCA ACA GTA TGG GCA-3' [SEQ ID NO:3], 3' primer: 5'-CGA AGA AGG AGA ATA GGG TTG-3' [SEQ ID NO:4]. The expected size of the amplified product is 540 bp. Amplification cycles consisted of 94° C. 5 min, 1 cycle; 94° C., 45 s, 55° C. 30 s, 72° C., 30 s, 35 cycles with a final extension at 72° C. for 7 min. To exclude contamination of the whole process, samples from sham-operated rats were handled in parallel.

The expression of the luciferase reporter gene was examined using a luciferase activity assay. Rats were sacrificed at 2 days post-injection by intracardiac perfusion with 0.1 M PBS (pH 7.4) following deep anesthesia. Six pairs of companion DRG around the injection site were collected and stored at −80° C. until processing. After adding PBS buffer (100 µl PBS per 50 mg tissue), each sample was homogenized by sonication for 10 seconds on ice, and then centrifuged at 13,000 rpm at 4° C. in a microcentrifuge. Ten microliters of the supernatant at room temperature was used for the luciferase activity assay employing an assay kit from Promega (Madison, Wis., USA). Measurements were made in a single-well luminometer (Berthold Lumat L B 9501) for 10 seconds. RLUs were normalized by the total protein concentration of the tissue extracts, measured with a protein assay kit (Bio-Rad, Hercules, Calif., USA).

For immunostaining, rats were sacrificed at 2 days post-injection. Following deep anesthesia, rats were perfused first with Ringer's solution followed by 2% paraformaldehyde in 0.1 M PBS (pH 7.4). After perfusion, 3 pairs of companion DRGs (L4 to L6) were removed and post-fixed in the same fixative for 2-4 hours before being transferred into 0.1 M PBS containing 15% sucrose. Frozen sections were cut at 30 µm thickness and mounted on coated slides. Sections were washed for 20 min in 0.1M PBS at pH 7.4 containing 0.2% Triton X-100, then blocked with 5% normal goat serum in PBS for 1 hour. Sections were then incubated overnight with primary antibodies polyclonal anti-luciferase (Promega; dilution 1:150) and monoclonal against neuron-specific nuclear protein (NeuN) (Chemicon International, USA; dilution 1:500). Sections were washed in 0.1 M PBS and further incubated with anti-rabbit IgG Tritc conjugate (Sigma-Aldrich, Inc., USA; dilution 1:100) and anti-mouse IgG Fitc conjugate (Sigma-Aldrich; dilution 1:100) for 1 hour. After incubation, sections were washed three times in PBS, mounted with DAKO fluorescent mounting medium and covered with coverslips. Control sections were incubated without primary antibodies. Sections were examined with an Olympus 500 confocal laser scanning microscope. Each section was initially scanned with a 488 nm laser line, and an emission filter BP 510-525, for the detection of Fitc fluorescein; and with a 543 nm laser line, and an emission filter LP 570, for the detection of Tritc fluorescein.

NGF Assay

Cos7 cells were used for in vitro transfection to test the gene expression from the plasmid pcDNA3.1/NGF. Cultured Cells were seeded in a 6-well plated at 60-70% confluency. After overnight incubation, the culture medium was replaced with Opti-MEM and an aliquot of 25 µl of PEI/DNA complexes containing 4 µg pcDNA3.1/NGF was added to each well. DNA/PEI complexes were incubated with the cells for 3 hours at 37° C. The medium was then replaced with fresh complete medium. After a further incubation for 24 hours, the cells and the medium were collected for NGF assays using a sensitive NGF ELISA Kit (Boehringer Mannheim). For the control group, pcDNA3-Luc was used instead of pcDNA3.1/NGF. For In vivo NGF expression analysis, 15 rats were used, 10 of which were used in the experimental group, 5 for each time interval at 3 and 7 days. The left 5 rats were used as normal controls. Four µg of pcDNA3.1/NGF or pcDNA3luc was complexed with PEI in 20 µl and injected into each rat as described above. DGR were collected and homogenised. The supernatants were used for NGF ELISA.

Evaluation of Nerve Regeneration

Four weeks post-operation, rats were anaesthetized again and the sciatic nerves together with NGCs were exposed and carefully isolated from the surrounding tissues. The nerve segment distal to the tube was pinched with a pair of forceps to identify the success of the nerve regeneration. Contraction of muscles on the back or retraction of the leg indicated the presence of regenerating sensory fibers in the pinching segment, while no response was taken as an indication of the absence of such fibers.

For histological examination, regenerated nerve cables within the NGCs were collected and fixed in 2.5% glutaradelyde in PBS buffer (pH=7.4) overnight. The subsequent fixation, embedding, sectioning, and staining procedures were the same as previously described (Xu et al. 2003, *Biomaterials* 24:2504). The distal segments of the regenerated nerve were then performed with semi-thin section and stained with Tolubine Blue for morphometric analysis. Seventeen transverse semi-thin section samples through the middle part of the 10-mm gaps were analyzed to determine the number of regenerated axons, fiber population and fiber diameter. Quantitative measurement and evaluation was carried out using Micro Image Lite™ (Olympus, Image Analysis Software). Areas of interest were selected for ultrathin sectioning. The ultrathin sections (100 nm) were stained with lead citrate, collected on copper mesh grids and examined in Philips EM 208s electron

Example 1

Gene Transfer to DRG via Lumbar Intrathecal Injection

Figure 2:
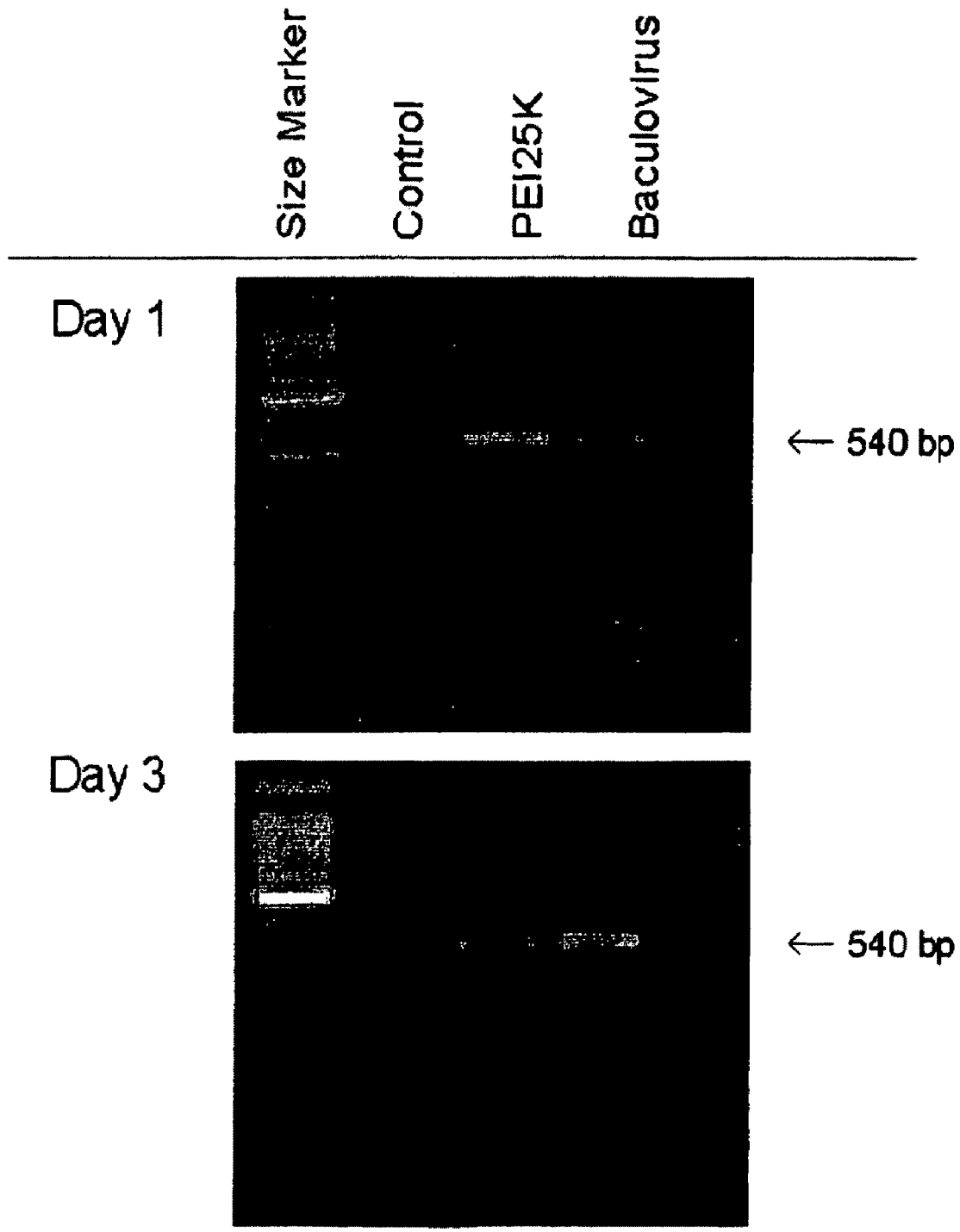
FIG. 2 shows transfection of DRG cells with PEI/DNA or baculovirus vectors encoding a firefly luciferase (Luc) gene one day (top panel) or three days (lower panel) after intrathecal injection. The 540 bp PCR fragment corresponds to a portion of the firefly luciferase gene.

We started with evaluating the uptake of gene vectors by DRG after intrathecal administration of baculovirus vectors or PEI/DNA complexes covalently labelled with Cy3. DRG close to the injection site were collected at 2 days post-injection and their sections were stained by anit-NeuN. Red Cy3 signals were detectable in the DRG, mainly in the cytoplasm of NeuN-positive cells under higher magnifications (FIG. 1); PCR analysis of the samples of DRG collected at day 1 and 3 post-injection revealed the existence of transported reporter genes in these PNS regions after the CNS injection (FIG. 2).

Figure 3:
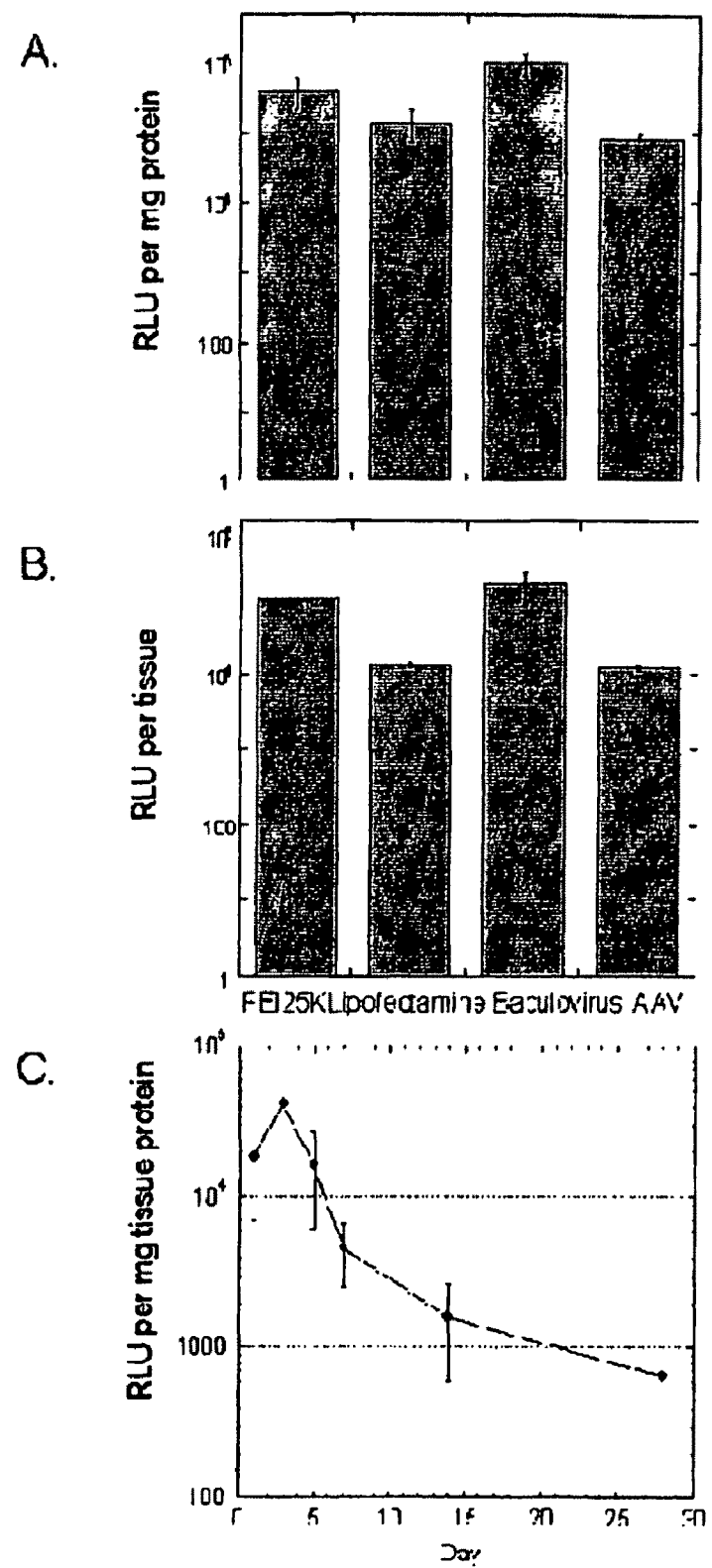
FIG. 3 shows luciferase expression from four different vectors with a CMV E/P promoter in DRG. Luciferase activities were measured at 2 days post-injection and are expressed in relative light units (RLU) per milligram of protein (FIG. 3A) or per tissue (FIG. 3B).
Figure 4:
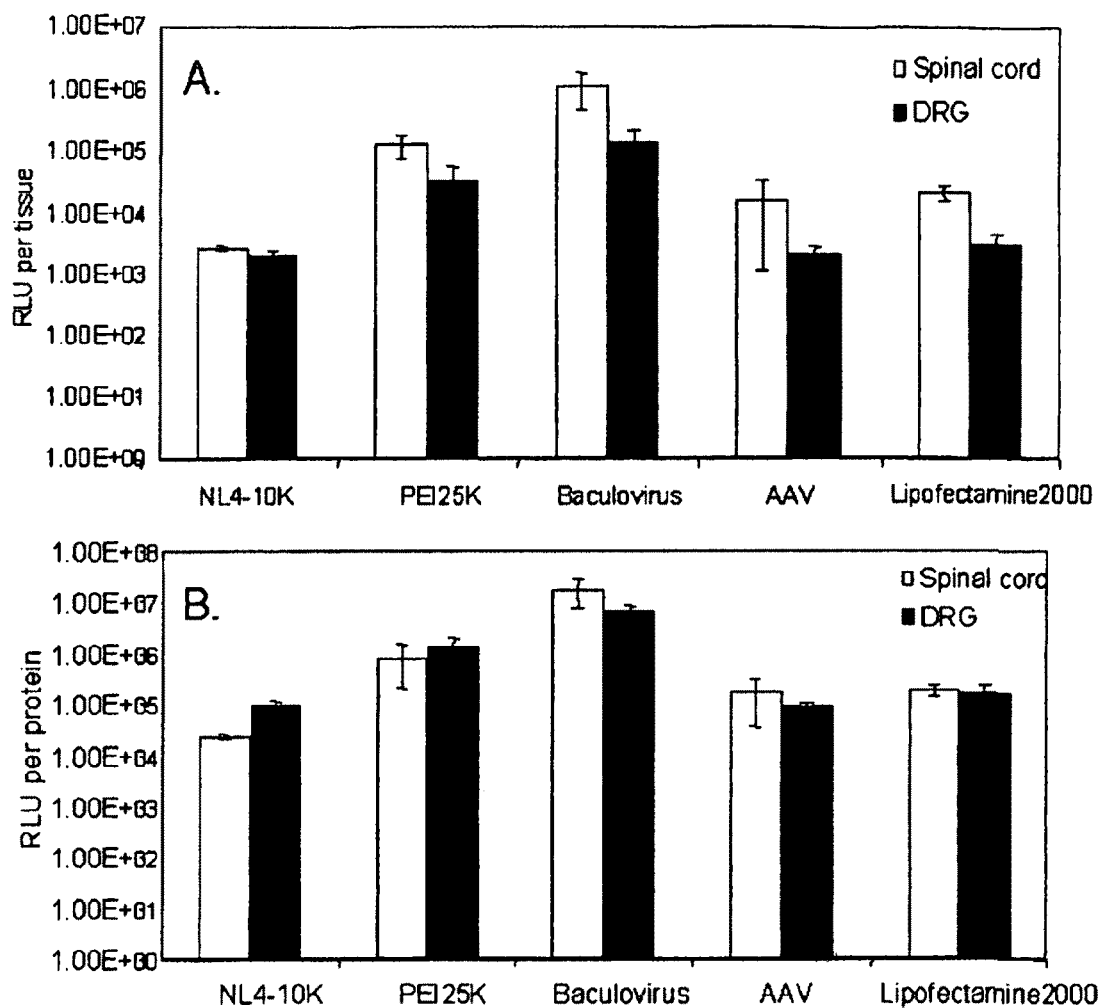
FIG. 4 shows luciferase expression from four different vectors with a CMV E/PDGF promoter in the spinal cord and the DRG. Luciferase activities were measured at 2 days post-injection and are expressed in relative light units (RLU) per tissue (FIG. 4A) or per milligram of protein (FIG. 4B).
Figure 5:
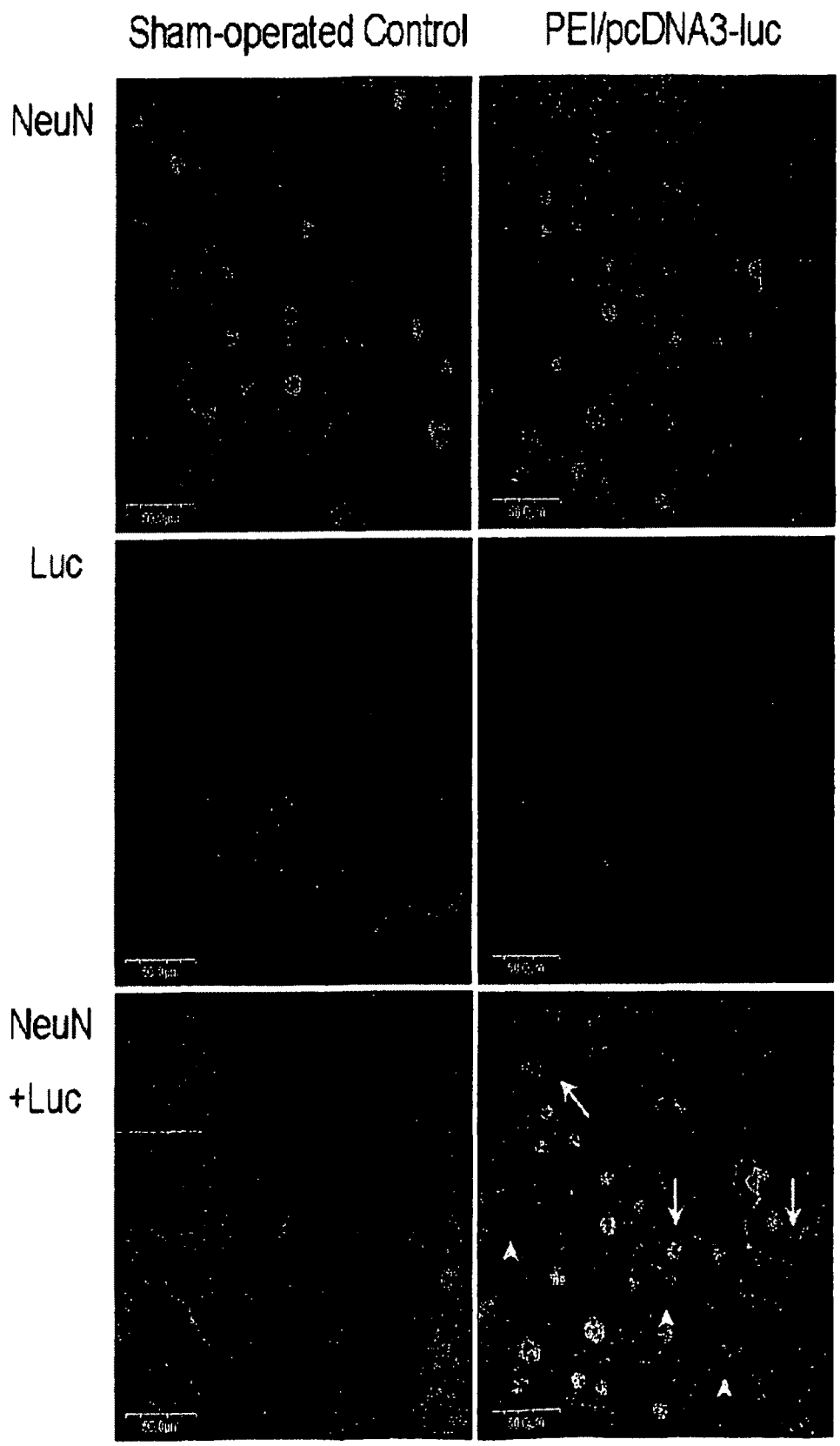
FIG. 5 shows confocal scanning microscope images of luciferase expression in neurons in DRG. Frozen sections of rat DRG collected 2 days after injection of PEI/DNA complexes were used for double immunostaining against luciferase to show transfected cells and against NeuN to show neurons. Most of the cells are well co-localized (NeuN+Luc, arrows), with a few of luciferase positive cells being not labeled by NeuN (arrow heads).

Four different types of gene delivery systems and vectors with a luciferase reporter gene, PEI/DNA complexes, lipofectamine/DNA complexes, baculovirus vectors and AAV-2 vectors, were tested for their effects in mediating transgene transfer into DRG cells. Two days after lumbar intrathecal injection, luciferase activities were easily detected in DRG cells for all types of the vectors (FIG. 3). In a time course study of transgenic luciferase expression from the PEI/DNA complexes, enzymatic activity could be detected as early as 1 day after injection, reached the peak at day 3, and then dropped over next several weeks, with a low activity still being detectable 4 weeks after injection (FIG. 3). The immunostaining of luciferase demonstrated that the protein detected in DRG was not limited on the epithelium, but also in ganglion cells. The double immunostaining for luciferase and the neuron-specific NeuN protein showed that most of the luciferase-positive cells in DRGs were also NeuN-positive, with only few luciferase-positive cells being non-neuronal cells (FIG. 5).

Example 2

NGF cDNA Transfection and Nerve Regeneration through Nerve Guide Conduits

Figure 6:
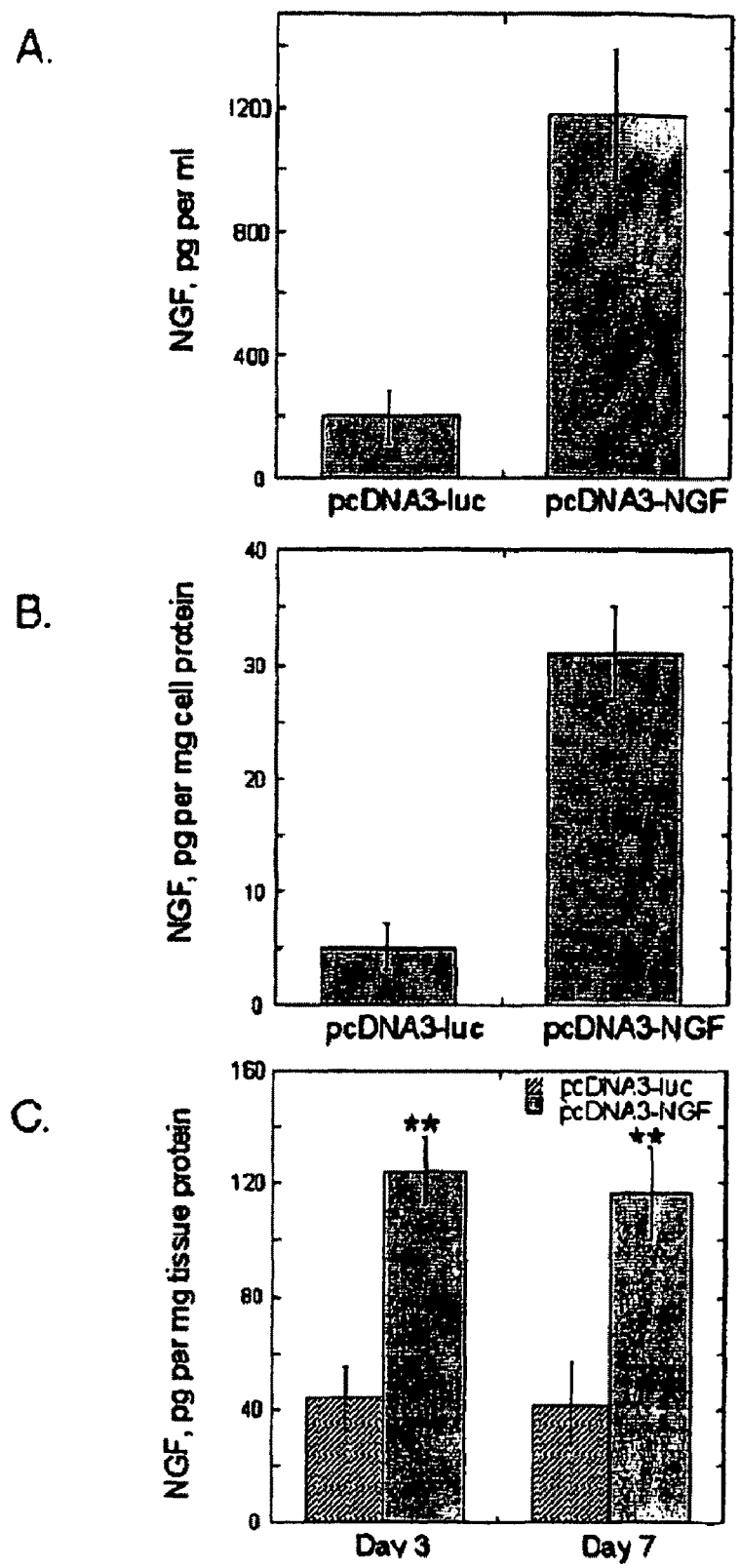
FIG. 6 shows NGF concentrations after in vitro (A, B) and in vivo (C) gene transfection. The concentrations of NGF in COS7 cell cultures are expressed per ml of culture medium (FIG. 6A) or per mg protein of cell lysate (FIG. 6B). The cells were collected 24 hours after in vitro transfection. DRG were collected 3 and 7 days after intrathecal injection of PEI complexes containing pcDNA3-NGF or a control plasmid pcDNA3-luc (FIG. 6C)

NGF, a neurotrophic factor predominantly acting on sensory and sympathetic neurons (Thorne, R. G., and Frey, W. H. II 2001, *Clin Pharmocokinet* 40:907), was selected to test the effects of its expression in DRG on peripheral nerve regeneration through nerve guide conduits (NGCs), a device widely tested in pre-clinical studies to repair nerve defects (Schmidt et al. 2003, *Ann. Rev. Biomed. Eng.* 293). We examined the expression of NGF cDNA from PEI-mediated gene delivery. After transfection of COS7 cells, the NGF concentration increased in the culture media, as detected in a sensitive ELISA, with a level of about 1 ng per ml and being 6 folds higher than the control (FIG. 6A). Similar increase was also observed when the cell lysate was analysed (FIG. 6B). After lumbar intrathecal injection of PEI/NGF cDNA complexes, the expression level of NGF in DRG was three-fold higher than the control and persisted for at least 7 days.

Example 3

Effects of NGF Expression on Nerve Regeneration

Figure 7:
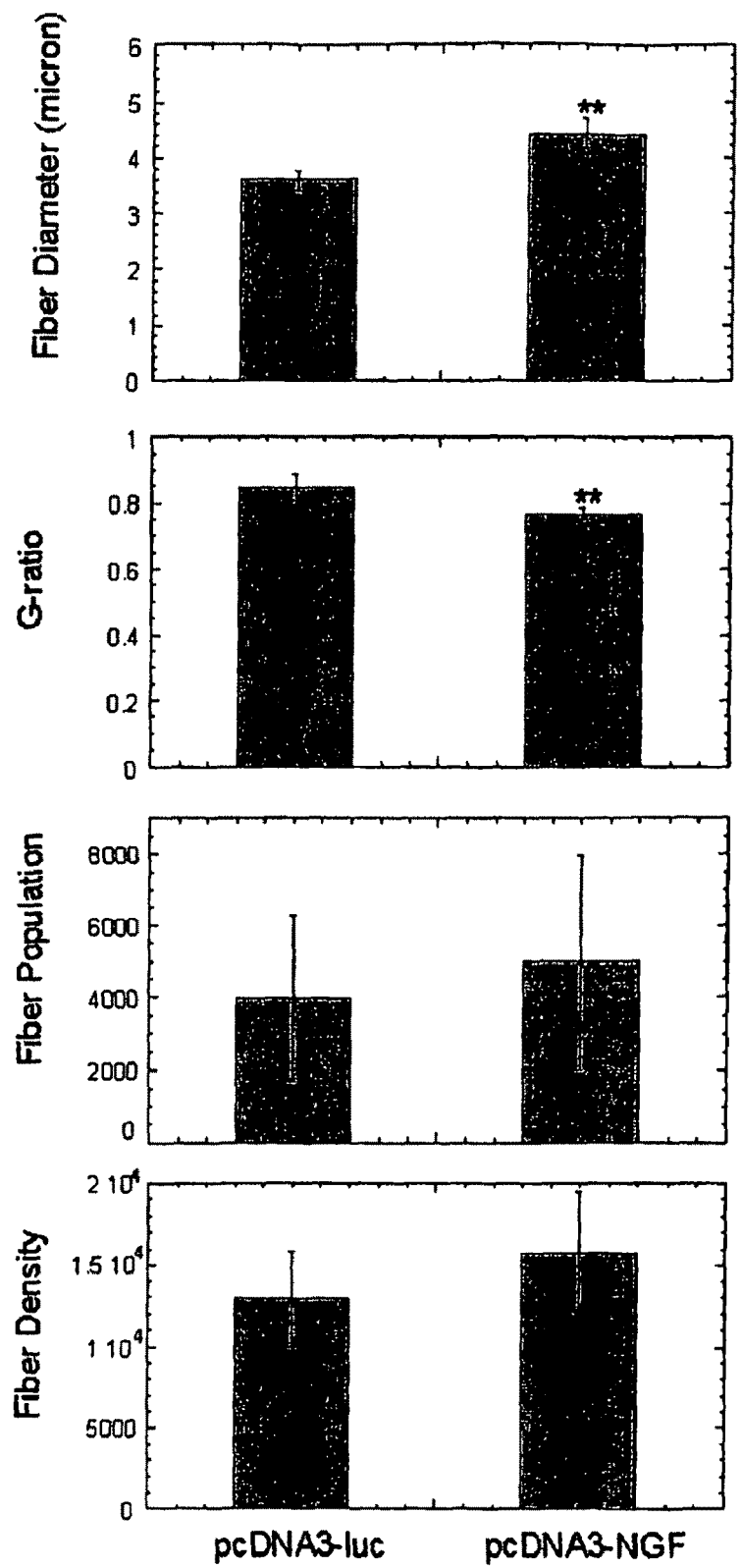
FIG. 7 shows morphometric analysis of nerve regeneration within NGCs 4 weeks after intrathecal injection. The samples from the PEI/pcDNA-NGF transfection group show larger diameter of fibers and a lower G ratio as compared with those from the control group (p<0.01). There is no significant difference between the two groups in terms of fiber population and density.

The successful rate of nerve regeneration through NGCs, as demonstrated in a pinch test, was 87% in the NGF group at 4 weeks post-operation, versus 67% in the control group. The regenerated tissue cables, which had bridged a 10-mm gap between two nerve stumps, could be found inside the conduits collected from the rats that were positive in the pinch test. Those tissue cables collected from NGCs of the NGF group showed improved regeneration qualities over their controls, with significant increase in the diameter of nerve fibers and decrease in G-ratio (Friende et al. 1982, *Brain Research* 235: 335), a ratio determined by axon diameter vs. myelinated fiber diameter (FIG. 7). In other two parameters examined, fiber population and density, ever though the certain improvement in the NGF group was visible, no statistically significant difference was found, probably due the big standard deviation (FIG. 7).

Figure 8:
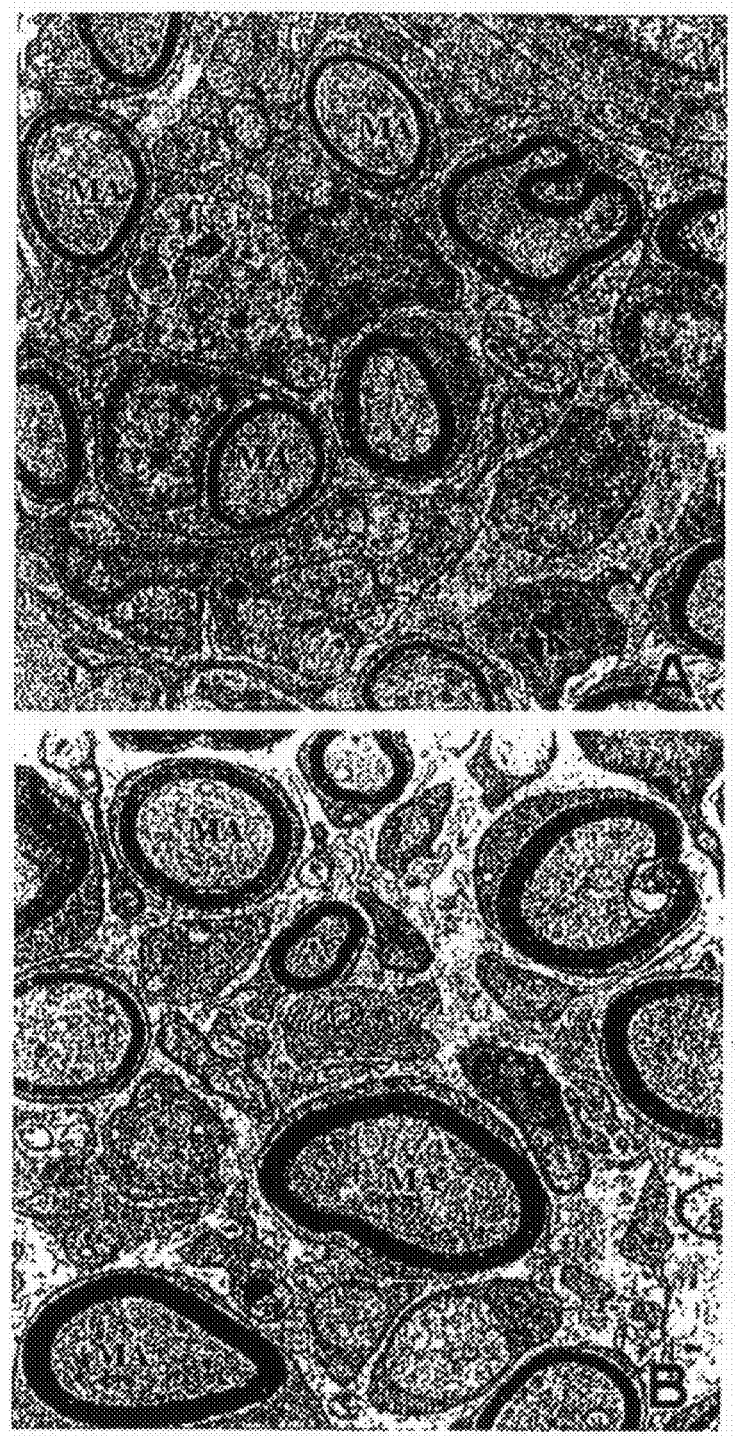
FIG. 8 shows electron microscope morphology of regenerated nerve fibers from the NGF transfected (B) and control (A) groups. Samples were collected 4 weeks after operation. MA: myelinated axons. Note larger axons with thicker myelin in the NGF group. The original magnification ×10000.

Morphological hallmarks of nerve regeneration were also examined by transmission electron microscopy. The regenerated nerve cables were centrally located within the conduits, surrounded by a fine epineurium. In both the NGF and control groups, the cables contained numerous of fascicles of regenerated myelinated as well as unmyelinated axons. The number, diameter and density of myelinated axons in the NGF group were more, lager and higher than those in the control group, respectively (FIG. 8). The myelin sheath presented in the NGF group was also much thicker than that in the control group (FIG. 8).

The present study thus demonstrates the positive influence of therapeutic NGF gene on the regeneration of transected sciatic nerves, providing one example of gene therapy for peripheral nerve regeneration. NGF is the first and best-characterized nerve-derived factor and acts on a relatively limited variety of neuronal population, including sympathetic and subpopulations of sensory neurons of peripheral nervous system, striatal and septal cholinergic neurons in the brain (Terenghi, G. 1999, *J. Anat.* 184:1). NGF is present at a very low concentration in the normal circumstances, and rapidly increases in the experimental nerve injury animal model. The proteins are produced mainly by the target tissue and Schwann cells in the distal stump of damaged nerves and then transported in a retrograde manner to the cell soma before acting on receptors on neurons and producing the neurotrophic effects. With peripheral neuropathy, such transport within diseased nerves may be negatively reduced or even totally blocked. An alternative means to maintain the transport mechanism thus uphold normal functions of affected neurons would be essential in treatment of peripheral neuropathy. Gene vectors delivered to DRG neurons by intrathecal injection do not require axonal transport to reach the cell body and could be beneficially utilized to support functions of neurons in DRG, thus slowing down or stopping degeneration processes of concerned axons.

NGF transfection in DRG, nerve regeneration, especially the diameter of new axons, was improved as demonstrated by both of the morphometric analysis and TEM analysis. The number of neurofilaments within axons has been considered as the key factor to control axonal diameter and in sensory neurons is probably subject to the regulation of NGF. Following peripheral nerve transection, nerve body size, axon diameter, neurofilament synthesis, and axonal transport of neurofilament are all reduced in sensory neurons. The transfection of NGF cDNA would up-regulate the expression of NGF protein and might have contributed to the enhancement of neurofilament synthesis and significant improvement in fiber diameter observed in the current study.

As can be understood by one skilled in the art, many modifications to the exemplary embodiments described herein are possible. The invention, rather, is intended to encompass all such modification within its scope, as defined by the claims.

What is claimed is

1. A method of delivering a nucleic acid into a neuronal cell in the peripheral nervous system of a host, the method comprising:
   (i) identifying a target neuronal cell in a dorsal root ganglion to which the nucleic acid is to be delivered; and
   (ii) administering a baculoviral vector comprising the nucleic acid into a site in the cerebrospinal fluid of the host, the site being sufficiently proximal to the dorsal root ganglion to deliver the nucleic acid into the cell body of the target neuronal cell.

2. A method of treating a peripheral neuropathy in a host, the method comprising:
   (i) identifying a target neuronal cell in a dorsal root ganglion affected by the neuropathy, to which target neuronal cell a therapeutic nucleic acid is to be delivered; and
   (ii) administering a baculoviral vector comprising the therapeutic nucleic acid into a site in the cerebrospinal fluid of the host, the site being sufficiently proximal to the dorsal root ganglion to deliver the nucleic acid into the cell body of the target neuronal cell.

3. A method of treating a transected peripheral nerve having a proximal and a distal stump in a host, the distal and proximal stumps being secured to a nerve guide conduit, the method comprising;
   (i) administering a baculoviral vector comprising a therapeutic nucleic acid to a dorsal root ganglion neuronal cell by administering the baculoviral vector at a site in the cerebrospinal fluid sufficiently proximal to the dorsal root ganglion neuronal cell to deliver the nucleic acid into the cell body of the dorsal root ganglion neuronal cell and results in nerve regeneration.

4. The method of claim 2 wherein the peripheral neuropathy is diabetic neuropathy, nerve compression or nerve transection.

5. The method of claim 1 wherein the nucleic acid comprises a coding sequence operably linked to a promoter.

6. The method of claim 5 wherein the promoter is a viral promoter.

7. The method of claim 6 wherein the viral promoter is a CMV promoter.

8. The method of claim 5 wherein the promoter is a neuron-specific promoter.

9. The method of claim 8 wherein the neuron-specific promoter is a PDGF β promoter.

10. The method of claim 5 wherein the promoter is operably linked to an enhancer.

11. The method of claim 10 wherein the enhancer is a CMV enhancer.

12. The method of claim 2 wherein the nucleic acid encodes a neurotrophic factor.

13. The method of claim 12 wherein the neurotrophic factor is a nerve growth factor.

14. The method of claim 13 wherein the nerve growth factor is NGF.

15. The method of claim 2 wherein the nucleic acid encodes an anti-apoptotic factor.

16. The method of claim 15 wherein the anti-apoptotic factor is bcl-2.

17. The method of claim 1 wherein the vector is administered by injection.

18. The method of claim 17 wherein the vector is administered by lumbar injection.

* * * * *

UNITED STATES PATENT AND TRADEMARK OFFICE
CERTIFICATE OF CORRECTION

| | | |
|---|---|---|
| PATENT NO. | : 8,034,331 B2 | Page 1 of 1 |
| APPLICATION NO. | : 11/795348 | |
| DATED | : October 11, 2011 | |
| INVENTOR(S) | : Shu Wang and Xu Wang | |

It is certified that error appears in the above-identified patent and that said Letters Patent is hereby corrected as shown below:

Title Page, Item (75) reads:

"[75] Inventors: Shu Wang, Singapore (SG); Xu Wang, Halifax (CA)"

Title Page, Item (75), should read:

--[75] Inventors: Shu Wang, Singapore (SG); Xu Wang, Singapore (SG)--

Signed and Sealed this
Fourteenth Day of February, 2012

David J. Kappos
*Director of the United States Patent and Trademark Office*